US012805728B1

(12) United States Patent
Kirby et al.

(10) Patent No.: US 12,805,728 B1
(45) **Date of Patent: *Nov. 24, 2026**

(54) NEAR-INFRARED SPECTROSCOPY FOR SENSING GLYCOGEN IN MUSCLE TISSUE

(71) Applicant: NIKE, Inc., Beaverton, OR (US)

(72) Inventors: Brett S. Kirby, Portland, OR (US); Vikram Malhotra, Portland, OR (US); Roger Schmitz, Hutchinson, MN (US)

(73) Assignee: Oura, Inc., San Francisco, CA (US)

( * ) Notice: Subject to any disclaimer, the term of this patent is extended or adjusted under 35 U.S.C. 154(b) by 1107 days.

This patent is subject to a terminal disclaimer.

(21) Appl. No.: 17/502,580

(22) Filed: Oct. 15, 2021

Related U.S. Application Data

(63) Continuation of application No. 15/417,016, filed on Jan. 26, 2017, now Pat. No. 11,147,481.

(Continued)

(51) Int. Cl.
*A61B 5/00* (2006.01)
*A61B 5/145* (2006.01)
(Continued)

(52) U.S. Cl.
CPC ........ *A61B 5/0075* (2013.01); *A61B 5/14532* (2013.01); *A61B 5/14546* (2013.01); *A61B 5/1455* (2013.01); *A61B 5/443* (2013.01); *A61B 5/4519* (2013.01); *A61B 5/4875* (2013.01); *A61B 5/6824* (2013.01);
(Continued)

(58) Field of Classification Search
CPC ... A61B 5/0059; A61B 5/0075; A61B 5/1455; A61B 5/4866; A61B 5/4869
See application file for complete search history.

(56) References Cited

U.S. PATENT DOCUMENTS 5,277,181 A 1/1994 Mendelson et al.
6,353,226 B1 * 3/2002 Khalil .................... G01N 21/49 600/323
(Continued)

FOREIGN PATENT DOCUMENTS

CN 1544947 11/2004
CN 1911172 A 2/2007
(Continued)

OTHER PUBLICATIONS

"International Application Serial No. PCT US2017 015174, International Search Report mailed Apr. 17, 2017", 7 pgs.
(Continued)

*Primary Examiner* — Puya Agahi
(74) *Attorney, Agent, or Firm* — Quinn IP Law

(57) ABSTRACT

A system, wearable device, and method include a light emitter configured to emit light at a first wavelength of between approximately 900 and 1000 nanometers and at a second wavelength of approximately 1350 nanometers, a first light detector spaced at a first distance from the light emitter, and a second light detector spaced at a second distance from the light emitter, the second distance approximately twice the first distance. At least one of hydration and glycogen of muscle tissue is determinable based on a relationship between backscatter light from the muscle tissue as detected by the second light detector and backscatter light from non-muscle tissue as detected by the first light detector.

26 Claims, 6 Drawing Sheets

Related U.S. Application Data

(60) Provisional application No. 62/287,286, filed on Jan. 26, 2016.

(51) Int. Cl.

| | |
|---|---|
| ***A61B 5/1455*** | (2006.01) |
| ***G01N 21/31*** | (2006.01) |
| ***G01N 21/3554*** | (2014.01) |
| ***G01N 21/359*** | (2014.01) |
| ***G01N 21/47*** | (2006.01) |

(52) U.S. Cl.

CPC ............ *A61B 5/7278* (2013.01); *A61B 5/742* (2013.01); *A61B 5/7475* (2013.01); *G01N 21/3151* (2013.01); *G01N 21/3554* (2013.01); *G01N 21/359* (2013.01); *A61B 2562/0238* (2013.01); *A61B 2562/0242* (2013.01); *A61B 2562/046* (2013.01); *G01N 2021/3181* (2013.01); *G01N 2021/4709* (2013.01)

(56) References Cited

U.S. PATENT DOCUMENTS

| | | | |
|---|---|---|---|
| 7,236,811 | B2 | 6/2007 | Schmitt |
| 8,180,419 | B2 | 5/2012 | Debreczeny et al. |
| 8,798,701 | B2 | 8/2014 | Izzetoglu et al. |
| 8,941,830 | B2 | 1/2015 | Schmitz |
| 11,147,481 | B1 | 10/2021 | Kirby et al. |
| 11,666,220 | B2 | 6/2023 | Kirby et al. |
| 2003/0204133 | A1 | 10/2003 | Harjunmaa et al. |
| 2004/0068163 | A1 | 4/2004 | Ruchti et al. |
| 2004/0260520 | A1 | 12/2004 | Braendle et al. |
| 2005/0226548 | A1 | 10/2005 | Durkin et al. |
| 2005/0256384 | A1 | 11/2005 | Walker et al. |
| 2006/0189861 | A1 | 8/2006 | Chen et al. |
| 2006/0276696 | A1 | 12/2006 | Schurman et al. |
| 2006/0281982 | A1 | 12/2006 | Grata et al. |
| 2007/0060819 | A1 | 3/2007 | Altshuler et al. |
| 2008/0081975 | A1 | 4/2008 | Agashe et al. |
| 2008/0221416 | A1 | 9/2008 | Baker |
| 2010/0145200 | A1* | 6/2010 | Mahadevan-Jansen .................... A61B 5/0091 600/476 |
| 2013/0023744 | A1 | 1/2013 | Benni |
| 2013/0096403 | A1 | 4/2013 | Dacso et al. |
| 2014/0155760 | A1 | 6/2014 | Ridder et al. |
| 2014/0171759 | A1 | 6/2014 | White et al. |
| 2014/0249390 | A1 | 9/2014 | Bernreuter et al. |
| 2014/0275869 | A1 | 9/2014 | Kintz et al. |
| 2016/0249836 | A1 | 9/2016 | Gulati et al. |
| 2021/0204816 | A1 | 7/2021 | Kirby et al. |

FOREIGN PATENT DOCUMENTS

| | | |
|---|---|---|
| CN | 103610467 | 3/2014 |
| CN | 109348727 | 2/2019 |
| CN | 115770016 | 3/2023 |
| DE | 102014003470 | 9/2015 |
| WO | 2017132404 | 8/2017 |

OTHER PUBLICATIONS

"International Application Serial No. PCT US2017 015174, Written Opinion mailed Apr. 17, 2017", 6 pgs.

"International Application Serial No. PCT US2017 015174, International Preliminary Report on Patentability mailed Aug. 9, 2018", 8 pgs.

"European Application Serial No. 17744907.1, Response filed Oct. 18, 2018 to Communication Pursuant to Rules 161 and 162 EPC mailed Sep. 18, 2018", 13 pgs.

"U.S. Appl. No. 15/417,016, Non Final Office Action mailed Jul. 25, 2019".

"European Application Serial No. 17744907.1, Extended European Search Report mailed Nov. 26, 2019", 10 pgs.

"U.S. Appl. No. 15/417,016, Response filed Dec. 26, 2019 to Non Final Office Action mailed Jul. 25, 2019", 13 pgs.

"U.S. Appl. No. 15/417,016, Final Office Action mailed Apr. 13, 2020".

"U.S. Appl. No. 15/417,016, Response filed Jun. 15, 2020 to Final Office Action mailed Apr. 13, 2020", 15 pgs.

"Chinese Application Serial No. 201780019817.5, Office Action mailed May 25, 2020", W English Translation, 23 pgs.

"U.S. Appl. No. 15/417,016, Advisory Action mailed Jun. 29, 2020", 2 pgs.

"European Application Serial No. 17744907.1, Response filed Jun. 23, 2020 to Extended European Search Report mailed Nov. 26, 2019", 8 pgs.

"U.S. Appl. No. 15/417,016, Response filed Sep. 14, 2020 to Advisory Action mailed Jun. 29, 2020", 16 pgs.

"U.S. Appl. No. 15/417,016, Non Final Office Action mailed Oct. 5, 2020", 10 pgs.

"Chinese Application Serial No. 201780019817.5, Response filed Sep. 24, 2020 to Office Action mailed May 25, 2020", w English claims, 46 pgs.

"U.S. Appl. No. 15/417,016, Examiner Interview Summary mailed Oct. 20, 2020".

"Chinese Application Serial No. 201780019817.5, Office Action mailed Jan. 28, 2021", w English Translation, 21 pgs.

"Chinese Application Serial No. 201780019817.5, Response filed Mar. 23, 2021 to Office Action mailed Jan. 28, 2021", w current English claims, claims not amended in response filed, 11 pgs.

"U.S. Appl. No. 15/417,016, Appeal Brief filed Jun. 3, 2021", 22 pages.

"Chinese Application Serial No. 201780019817.5, Decision of Rejection mailed May 24, 2021", With English translation, 28 pages.

"U.S. Appl. No. 15/417,016, Advisory Action mailed Jun. 14, 2021", 2 pgs.

"U.S. Appl. No. 15/417,016, Notice of Allowance mailed Jun. 23, 2021", 8 pgs.

"Chinese Application Serial No. 201780019817.5, Response filed Aug. 24, 2021 to Decision of Rejection mailed May 24, 2021", With English claims, 44 pages.

"Chinese Application Serial No. 201780019817.5, Office Action mailed Dec. 16, 2021", With English translation, 19 pgs.

Williams, C, "Influence Of Nutrition On Exercise Capacity", Jan. 1, 1992, (Jan. 1, 1992), 4 pgs.

Ye, Yang, "Effect of skin and fat layers on the spatial sensitivity profile of continuous wave diffuse reflectance near-infrared spectra", Visual Communications and Image Processing; 20-1-2004-Jan. 20, 2004; San Jose,,vol. 6007, (Nov. 9, 2005), 9.

"Chinese Application Serial No. 201780019817.5, Response filed May 5, 2022 to Office Action mailed Dec. 16, 2021", w English claims, 53 pgs.

"U.S. Appl. No. 16/071,383, Non Final Office Action mailed Jun. 9, 2022", 16 pgs.

"Chinese Application Serial No. 201780019817.5, Decision of Rejection mailed May 19, 2022", With English machine translation, 23 pgs.

"U.S. Appl. No. 16/071,383, Response filed Dec. 9, 2022 to Non Final Office Action mailed Jun. 9, 2022", 12 pgs.

"U.S. Appl. No. 16/071,383, Notice of Allowance mailed Feb. 10, 2023", 7 pgs.

"U.S. Appl. No. 16/071,383, Corrected Notice of Allowability mailed Apr. 26, 2023", 2 pgs.

"Chinese Application Serial No. 201780019817.5, Response filed Aug. 12, 2022 to Decision of Rejection mailed May 19, 2022", w English claims, 47 pgs.

"European Application Serial No. 17744907.1, Communication Pursuant to Article 94(3) EPC mailed Nov. 18, 2022", 9 pgs.

* cited by examiner

NEAR-INFRARED SPECTROSCOPY FOR SENSING GLYCOGEN IN MUSCLE TISSUE

PRIORITY

This application claims the benefit of priority to U.S. Provisional Patent Application No. 62/287,286, entitled "NEAR-INFRARED SPECTROSCOPY FOR SENSING CHARACTERISTICS OF MUSCLE TISSUE," filed Jan. 26, 2016, which is incorporated herein by reference in its entirety.

TECHNICAL FIELD

The subject matter disclosed herein generally relates to the use of near-infrared spectroscopy for the sensing of characteristics of muscle tissue.

BACKGROUND

Near-infrared spectroscopy (NIRS) utilizes particular frequencies of near-infrared light to diagnose various conditions of tissue, such as blood oxygen content and hemoglobin among other diagnostics. Conventional NIRS applications may shine near-infrared light of one or more wavelengths into subject tissue. The backscatter of the light off of various constituent components of the tissue and associated fluids may then be detected by a photoreceptor and the content of the tissue/fluids may be inferred based on the amount and characteristics of the light detected.

BRIEF DESCRIPTION OF THE DRAWINGS

Some embodiments are illustrated by way of example and not limitation in the figures of the accompanying drawings.

DETAILED DESCRIPTION

Figure 1:
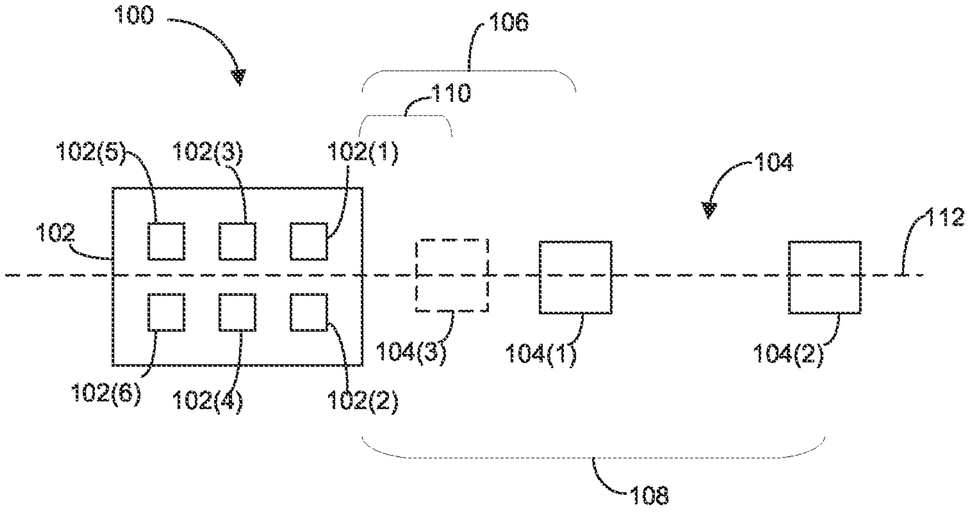
FIG. 1 is a positional diagram of components of a system configured to detect muscle tissue hydration using NIRS, in an example embodiment.

Example methods and systems are directed to NIRS for sensing characteristics of muscle tissue. Examples merely typify possible variations. Unless explicitly stated otherwise, components and functions are optional and may be combined or subdivided, and operations may vary in sequence or be combined or subdivided. In the following description, for purposes of explanation, numerous specific details are set forth to provide a thorough understanding of example embodiments. It will be evident to one skilled in the art, however, that the present subject matter may be practiced without these specific details.

Conventionally, NIRS applications have been utilized for analyses of tissue or fluids that don't discriminate between tissues of varying depths. For instance, blood oxygen and hemoglobin content may be analyzed from tissue from one to three millimeters below the surface of the skin, but such an analysis may not discriminate effectively between characteristics at such shallow depths and characteristics at deeper depths. Because the backscatter light from tissue only a few millimeters below the skin travels similarly short distances, the photoreceptor may be placed either co-located with the light emitter(s) or within millimeters of the light emitter(s).

Moreover, conventionally, muscle tissue is typically analyzed for various characteristics via invasive procedures, such as biopsy procedures. Thus, to determine characteristics of muscle tissue, such as glycogen and water levels, tissue samples are collected and then shipped to a lab for analysis. Consequently, muscle tissue analysis can be relatively expensive and time consuming.

Alternative, non-invasive techniques for measuring tissue parameters of muscle tissue have been developed, including various ultrasound techniques. However, ultrasound techniques rely on equipment which is typically immobile, complicated to use, and which may require the use of gels to limit air gaps between the ultrasound transducer and the skin. Consequently, even if ultrasound machines could be utilized under certain circumstances, ultrasound machines have tended to be impractical both in terms of cost and conditions of use.

A system has been developed which utilizes NIRS to determine glycogen levels of tissue, such as a muscle layer of the tissue, that discriminates between characteristics of the muscle layer and characteristics of other layers of the tissue. The characteristics include glycogen levels and hydration levels, among other potential characteristics. The system utilizes particular light wavelengths as well as a specified positional relationship between the light emitters and the light detectors to obtain backscatter from particular tissue and fluids to identify glycogen and/or hydration of muscle tissue. In particular, the system is configured to discriminate between water and/or associated glycogen content of muscle tissue and water content of non-muscle tissue.

In an example, the system utilizes multiple NIRS wavelengths to obtain an assessment of volumetric hydration in multiple layers of tissue. The detected light from the multiple NIRS wavelengths are then differentiated to determine isolated hydration in muscle tissue. The isolated hydration in muscle tissue may then be utilized to determine a glycogen level of the muscle tissue. The glycogen level and/or the hydration level may be utilized in diagnostics of the muscle tissue, including muscle contractile function and overall muscle fatigue.

The system is based, among other bases, on a recognition of the potential benefits of utilizing NIRS for discriminating between characteristics of deep and shallow tissue layers. Among the benefits is the capacity to create a portable, wearable device which may be utilized during physical activity. Such a device may also provide ease of use and allow such a device to be utilized by users who lack specific training or knowledge of medical equipment.

FIG. 1 is a positional diagram of components of a system 100 configured to detect muscle tissue hydration using NIRS, in an example embodiment. The system 100 includes a light emitter 102 and multiple light detectors 104 arranged in a specified configuration with respect to one another. In various examples, the system 100 is a single wearable device configured to be worn on the arm or other portion of the anatomy of a user. However, it is to be understood that any combination of discrete devices that include the light emitter 102 and light detectors 104 in the specified positional relationship. A wavelength range or optical window of approximately six hundred (600) nanometers to approximately one thousand four hundred (1400) nanometers tends to provide sensitivity to tissue down to muscle tissue by the system 100, as illustrated herein. Such an optical window is broader than typical in NIRS applications.

In various examples, the light emitter 102 includes or is made up of multiple individual elements, in an example light emitting diodes (LEDs) configured to emit near-infrared light at specified wavelengths. In such examples, a first LED 102(1) is configured to emit light at a first wavelength over a range of approximately nine hundred (900) nanometers to one thousand (1000) nanometers. In an example, the first LED 102(1) is configured to emit light at a first wavelength of approximately nine hundred seventy (970) nanometers. Further, in such examples, a second LED 102(2) is configured to emit light at a second wavelength over a range of approximately one thousand three hundred (1300) nanometers to approximately one thousand four hundred (1400) nanometers. In an example, the second LED 102(2) is configured to emit light at a second wavelength of approximately one thousand three hundred ten (1310) nanometers. As will be disclosed in detail herein, the light from the first and second LEDs 102(1), 102(2) may be primarily or entirely utilized to determine muscle glycogen levels and/or hydration content.

Figure 2:
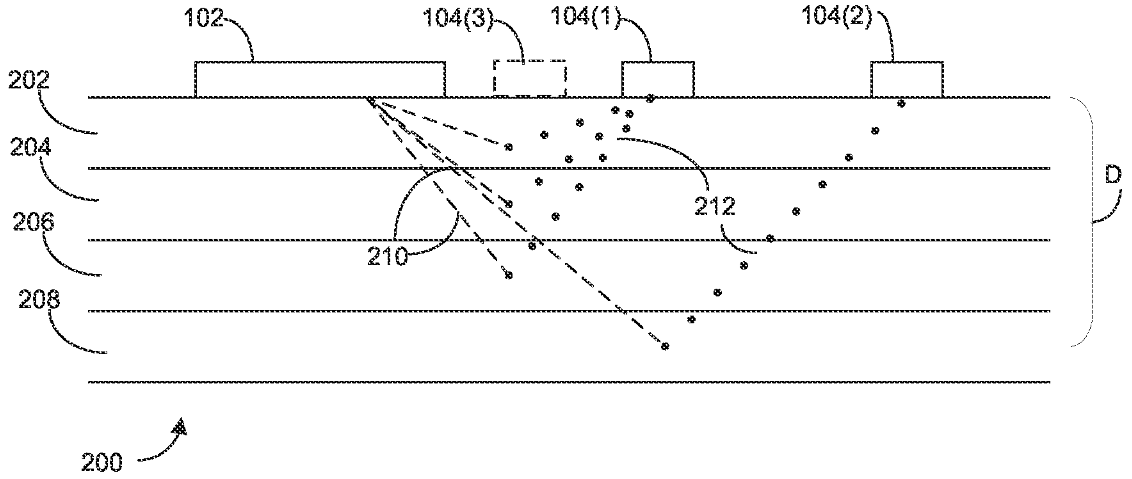
FIG. 2 is an abstract profile of a system in relation to tissue, in an example embodiment.

In various examples, the system 100 further includes a third LED 102(3), a fourth LED 102(4), a fifth LED 102(5), and a sixth LED 102(6) variously configured to emit light at wavelengths between approximately six hundred sixty (660) nanometers to eight hundred twenty (820) nanometers and, in an example, from between approximately six hundred eighty (680) nanometers to eight hundred (800) nanometers. In various examples, the third LED through sixth LEDs 102(3), 102(4), 102(5), 102(6) are configured to emit light conventionally used in the detection of hemoglobin or oxygen levels of hemoglobin but which may, in various examples, be utilized in the detection of water for muscle hydration and/or associated glycogen molecules In various alternative examples, the first LED 102(1) and the second LED 102(2) are configured to emit light at approximately nine hundred seventy (970) nanometers and one thousand three hundred and ten (1310) nanometers, respectively, while the third LED 102(3) is configured to emit light at approximately six hundred eighty (680) nanometers, the fourth LED 102(4) is configured to emit light at approximately eight hundred (800) nanometers, fifth LED 102(5) is configured to emit light at approximately nine hundred thirty (930) nanometers, and sixth LED 102(6) is configured to emit light at approximately one thousand two hundred and ten (1210) nanometers. For all of the wavelengths disclosed herein, it is noted and emphasized that the wavelengths may vary from 0.5 nanometers to twenty-five (25) nanometers and still be considered approximately the recited wavelength. In various examples, the system 100 may be configured to measure a thickness of a fat layer, a water content of an epidermis layer, a water content of a muscle layer, percentage oxygenation in a muscle layer, and total hemoglobin in a muscle layer, as illustrated in FIG. 2. The system 100 may tend to filter out or otherwise be substantially insensitive to total hemoglobin in the epidermis layer, percentage oxygenation in an epidermis layer, and melanin concentration.

The individual LEDs 102(1), 102(2), . . . may optionally include componentry to focus or direct the light output of the light emitter 102. In an example, individual LEDs 102(1), 102(2), . . . include a flexible lightguide film that allows for specification of an angle at which light is emitted from the LEDs 102(1), 102(2), . . . . The lightguide film may be one (1) millimeter thick or less.

While the illustrated example illustrates a particular example of the light emitter 102, i.e., the first and second LEDs 102(1), 102(2), and four optional light emitters 102(3), 102(4), 102(5), 102(6), it is to be recognized and understood that any combination of light emitting elements that may produce the specified wavelengths may be utilized. Thus, for instance, if a single light emitting element was configured to produce all of the specified wavelengths then the individual light emitting elements 102(1), 102(2) . . . may be replaced with a single light emitting element providing all of the wavelengths produced by the light emitter 102. Similarly, if a single light emitting element could produce both 970 nanometer light and 1310 nanometer light then the single light emitting element may replace the first and second LEDs 102(1), 102(2) while leaving the optional third through sixth LEDs 102(3), 102(4), 102(5), 102(6) in the system 100. Additionally or alternatively, a single light emitting element that does not produce more than one wavelength at a time may switch between and produce individual wavelengths over time, e.g., by producing 970 nanometer light followed by 1310 nanometer light, then back to 970 nanometer light, and so forth.

The system 100 further includes the light detectors 104. In an example, the light detectors 104 are photodiodes that produce a signal output indicative of light detected. In various examples, current of the photodiodes may be integrated together over milliseconds or seconds to amplify the signal output from the photodiodes that reflects muscle hydration. In an example, a first light detector 104(1) is positioned at a first distance 106 approximately 12.5-15.0 millimeters or 0.5 inches from the light emitter 102. In an example, a second light detector 104(2) is positioned at a distance 108 of approximately twenty-five (25) to thirty (30) millimeters or 1.0 inches from the light emitter 102. In an example, a third light detector 104(3) is optionally positioned at a distance 110 of approximately 6.25 millimeters along a common axis 112 with the light emitter 102, the first light detector 104(1), and the second light detector 104(2).

While the system 100 is illustrated with one light emitter 102 and one set of light detectors 104, it is to be recognized and understood that the system 100 may incorporate multiple light emitters 102 and/or multiple sets of light detectors 104. In various examples, two or more of each of the light emitter 102 and light detectors 104 may allow for glycogen and/or hydration measurements or measurements of other characteristics of the muscle tissue to be taken concurrently or essentially concurrently at multiple locations within the same muscle tissue, allowing for potentially a more complete assessment of the glycogen, hydration, or other characteristic of the muscle tissue than may be obtained with a single light emitter 102 and set of light detectors 104. In various examples, the data from multiple sets of light detectors 104 may be averaged or may be separately reported and displayed to a user. It is further noted that the light form a single light emitter 102 may be utilized by multiple sets of light detectors 104, i.e., where the light from the light emitter 102 is not focused directionally, multiple light detectors 104 may detect the light and make muscle characteristic assessments thereby.

FIG. 2 is an abstract profile of the system 100 in relation to tissue 200, in an example embodiment. The tissue 200 is conventional human skin and/or tissue close to the skin that may be expected to be found on the arm of a user of the system 100. The tissue 200 includes, at a high level, an epidermis layer 202, a dermis layer 204, a fat layer 206, and a muscle layer 208. As the light emitter 102 emits light 210, the light scatters off the various layers 202, 204, 206, 208. Resultant backscatter light 212 is detected by the individual light detectors 104.

In an example, the relatively shallower, non-muscle layers, such as the epidermis layer 202, the dermis layer 204, and the fat layer 206 have hydration levels that are generally indicative of general body hydration instead of local hydration levels. By contrast, the muscle layer 208 may have hydration levels specific to the muscle layer 208 itself in proximity of the system 100. In general, the light detectors 104 are positioned within the system 100 such that the first light detector 104(1) detects backscatter light 212 from the non-muscle layers while the second light detector 104(2) detects backscatter light 212 from various layers including but not limited to the muscle layer 208 and, in an example, all of the layers 202, 204, 206, 208. Utilizing the system 100 and example dimensions provided above, the backscatter light 212 detected at a depth D of approximately 12.5 millimeters from a surface 214 of the epidermis layer 202.

It is noted, however, that the illustration of FIG. 2 provides a depiction of light 210 and backscatter light 212 that may emphasize the primary mechanism by which light is detected by the first light detector 104(1) and the second light detector 104(2), but that light 210 and backscatter light 212 from any layer 202, 204, 206, 208 may be detected by either of the first light detector 104(1), the second light detector 104(2), and the optional third light detector 104(3). In fact, though the light 210 and backscatter light 212 patterns illustrated in FIG. 2 may be useful models for understanding what light tends to be detected by the first light detector 104(1) and the second light detector 104(2), the light detected by each light detector 104, including the third light detector 104(3), may include light 210 and backscatter light 212 from each layer 202, 204, 206, 208.

As such, examples of the system 100 that include the third light detector 104(3) may utilize principles known in the art to receive general light intensity values, access a predetermined look up table of light intensity values, integrating a Beer-Lambert equation over various wavelengths, such as the six wavelengths disclosed herein, and determine a tissue parameter based on a closest match between measured and simulated data. Such a mechanism is disclosed, for instance, in U.S. Pat. No. 8,941,830, "MEASURING TISSUE PARAMETER USING TABLE OF LIGHT ATTENUATION DATA", which is incorporated by reference herein in its entirety and is referred herein as "the '830 patent". However, in contrast to the applications of such principles in prior disclosures, rather than considering the presence of water a confounding factor in the detection of another tissue parameter, the instant system 100 may utilize the third light detector 104(3) and the six disclosed light wavelengths to detect the presence of water specifically in the muscle layer 208, to the substantial exclusion of water in other tissue layers 202, 204, 206, to then determine the glycogen level of the muscle layer 208.

The muscle tissue of the muscle layer 208 conventionally includes glycogen molecules which attach with at least one water molecule. In general, as glycogen depletes from the muscle tissue the water associated with the glycogen detaches from the glycogen and similarly leaves the muscle tissue, resulting in a reduction in the hydration of the muscle tissue. In examples of the system 100 not including the third light detector 104(3), by comparing the light, including the backscatter light 212, detected by the first and second light detectors 104(1), 104(2), effects of water detected in the non-muscle layers 202, 204, 206 may be identified and cancelled out of the light detected by the second light detector 104(2), substantially leaving backscatter light 212 generated based on glycogen and/or water in the muscle layer 208. As disclosed herein, examples of the system 100 that include the third light detector 104(3) may use similar techniques to that and others disclosed herein to determine the glycogen level of the muscle tissue.

In various examples, the identification of water in muscle tissue not only acts as an index for overall hydration status, but may also provide knowledge with respect to skeletal muscle glycogen concentrations. In such examples, for each gram of skeletal muscle glycogen, from three (3) to four (4) grams of water also tends to exist in the muscle tissue. On the basis of such a ratio, glycogen levels may be assessed via hydration sensing using the system 100.

A glycogen and/or hydration level of the muscle layer 208 may be indicative of muscle fatigue as well as muscle injury (and, by extension, muscle recovery from injury). Acute reductions in skeletal muscle glycogen (resultant during intense or prolonged exercise, for example) are mechanistically linked to impaired muscle contractile function and overall muscular fatigue. In various circumstances, glycogen is compartmentalized into distinct pools within skeletal muscle. Such discrete pools may contribute to intracellular calcium handling, and thus ultimately the force generated during muscle contraction. The assessment of glycogen from multiple discrete locations/departments may support the detection of individual glycogen pools; as such, the system 100 my incorporate multiple light emitters 102 and detectors 104 in discrete locations, as disclosed herein.

In exercise conditions to which skeletal muscle undergoes micro-damage, glycogen resynthesis may be compromised, thus further hampering or reducing performance during subsequent exercise activities. Additionally, because, for instance, nutritional intervention may not necessarily fully replenishment glycogen in exercise-induced damaged muscle in a similar time course to undamaged muscle, the system 100 and resultant analysis for glycogen assessment may also provide insight with regards to the degree of muscle injury/damage present. In various examples, as the glycogen content and/or hydration level of the muscle layer 208 decreases gradually, such as during activity, the fatigue of the muscle tissue may be inferred. The system 100 may access or may include an activity sensor, such as an accelerometer, to identify or further identify activity and utilize such data to determine muscle fatigue. Similarly, an inability to retain water in the muscle tissue of the muscle layer 208 relative to a baseline hydration value may be indicative of muscle injury while a return to the baseline hydration level may be indicative of muscle recovery.

Additionally, before-and-after assessments of muscle hydration and fatigue may be made by comparing muscle hydration and/or glycogen levels before an activity with hydration and/or glycogen levels after the activity. The system 100 may include an ability to input a desired activity intensity/muscle fatigue against which the actual muscle fatigue as determined may be compared for feedback to the user regarding whether or not an activity intensity goal was met. Such assessments may also be made during an activity to assess the efficacy of fluid and nutrient intake during an activity and to advise a user as to whether or not additional fluid or nutrients should be taken to sustain performance. Such assessments may also be made following an activity to assess the efficacy of after-activity meals and fluid intake by comparing the recovery of the muscle tissue against a desired baseline.

In various examples, a baseline body hydration level may be determined by measuring the water content of non-muscle layers 202, 204, 206 and/or the muscle layer 208, in various examples in relation to body weight of the wearer of the system 100. Ongoing measurements using the system 100 may provide comparative assessments of hydration levels in either or both of the non-muscle layers 202, 204, 206 and/or the muscle layer 208 over time.

Figure 3:
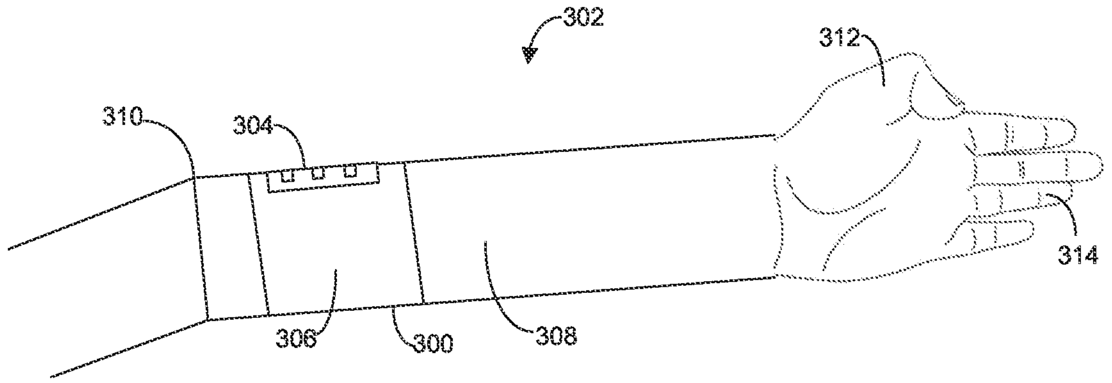
FIG. 3 is a depiction of a wearable device implementing a system, as worn on the arm of a user, in an example embodiment.

FIG. 3 is a depiction of a wearable device 300 implementing the system 100, as worn on the arm 302 of a user, in an example embodiment. The wearable device 300 includes the system 100 as implemented on an electronics module 304. A fixation element 306 is coupled to the electronics module 304 and is configured to secure the wearable device 300 in a desired orientation on the arm 302 of the user. In an example, the fixation element 306 is an elastic band, but it is to be recognized and understood that any suitable fixation element 306, including a strap, clasp, or other device may be utilized as desired.

In the illustrated example, the wearable device 300 is configured to be secured to a forearm 308 of the arm 302 proximate the elbow 310. The common axis 112 (FIG. 1) is configured to be substantially in line with the thumb 312 and fingers 314 in an extended position. However, it is to be recognized that the system 100 may be configured to function as disclosed herein in a variety of locations on the arm 302 or elsewhere on the user, such as over quadriceps muscles and deltoid muscles. In various examples, the wearable device 300 and the system 100 in general may be configured to operate over any of a variety of muscle tissue for which information regarding muscle hydration, injury, or recovery may be desired.

The principles disclosed herein regarding the physical layout of the system 100 may be applied to various alternative targeted muscle tissue. Thus, for instance, the dimensions illustrated in FIG. 1 may be adjusted dependent on the depth of the muscle tissue to be measured. For instance, in an example, the distance 108 between the light emitter 102 and the second light detector 104(2) may be approximately twice that of the depth of the muscle tissue to be measured.

Figure 4:
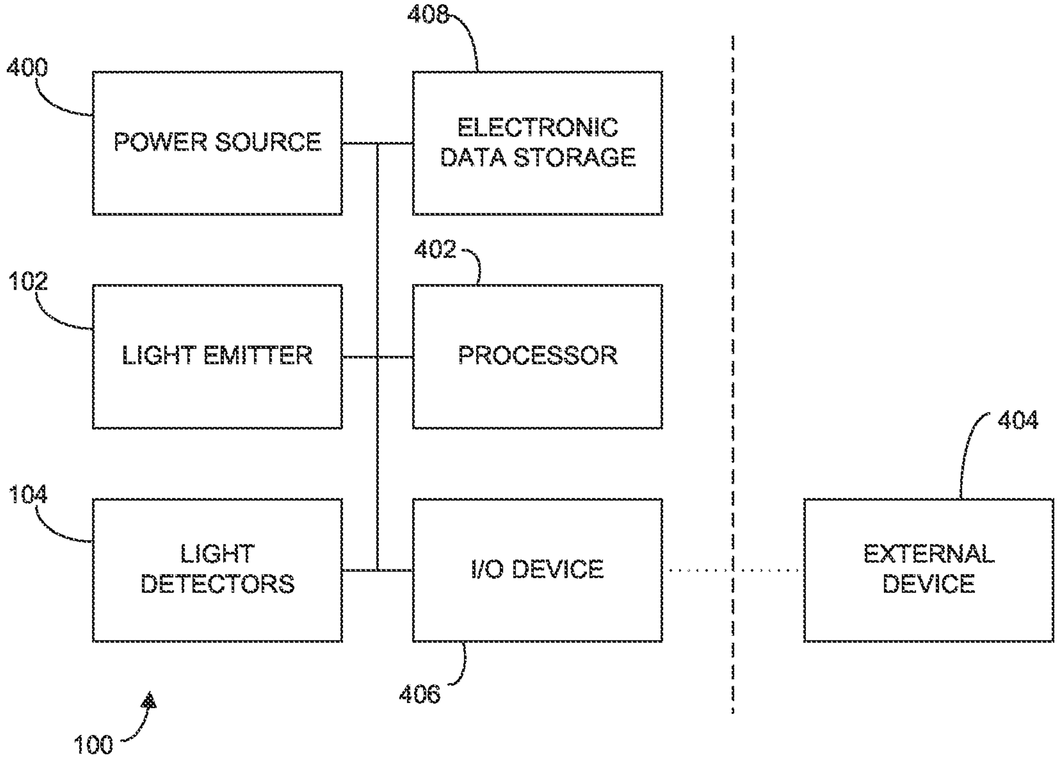
FIG. 4 is a block diagram of a system, in an example embodiment.

FIG. 4 is a block diagram of the system 100, in an example embodiment. In addition to the light emitter 102 and the light detectors 104, the system includes a power source 400 coupled to the light emitter 102 and the light detector 104. The power source 400 may be a battery, either rechargeable or non-rechargeable, or other suitable energy storage device, such as a supercapacitor. The power source 400 may further include circuitry for recharging the power source 400, such as a battery recharger or energy harvesting circuitry.

The system 100 further includes a processor 402 communicatively coupled to the light emitter 102 and light detectors 104. In the illustrated example, the processor 402 is a component of the wearable device 300 and is directly coupled to the light emitter 102 and the light detectors 104. Alternatively, the processor 402 is a remote processor in an external computing device 404, such as a personal computer or laptop computer, a mobile computing device, such as a smartphone or tablet computer, or other computing device that includes a processor. Where the processor 402 is a component of the wearable device 300, the processor 402 may function both as a controller to control the operation of the light emitter 102 and light detectors 104 as well as to process the signals transmitted from the light detectors to determine muscle hydration. Where the processor 402 is a remote processor a separate analog and/or digital controller may be included in the mobile device 300 to control the operation of the light emitter 102 and light detectors 104.

The system 100 further includes an input/output (I/O) device 406, such as a wireless transceiver or a wired data port. The I/O device 406 is configured to communicate with the external computing device 404. Where the processor 402 is a component of the wearable device 300, data from the processor 402 is transmitted via the I/O device 406 for communication via a display or other user interface device. Where the processor 402 is a component of the external computing device 404, the I/O device 406 transmits data obtained from the light detectors 104 to the processor 402 for processing.

The system 100 further optionally includes an electronic data storage 408 configured to store data related to the characteristic of the muscle tissue, such as hydration data and glycogen data, as disclosed herein. The processor 402 may access the data stored in the electronic data storage 408 to compare data obtained at different times to analyze changes in the characteristics over time. Such analysis may include the setting of baseline hydration or glycogen characteristics and the change in hydration or glycogen during an activity.

Figure 5:
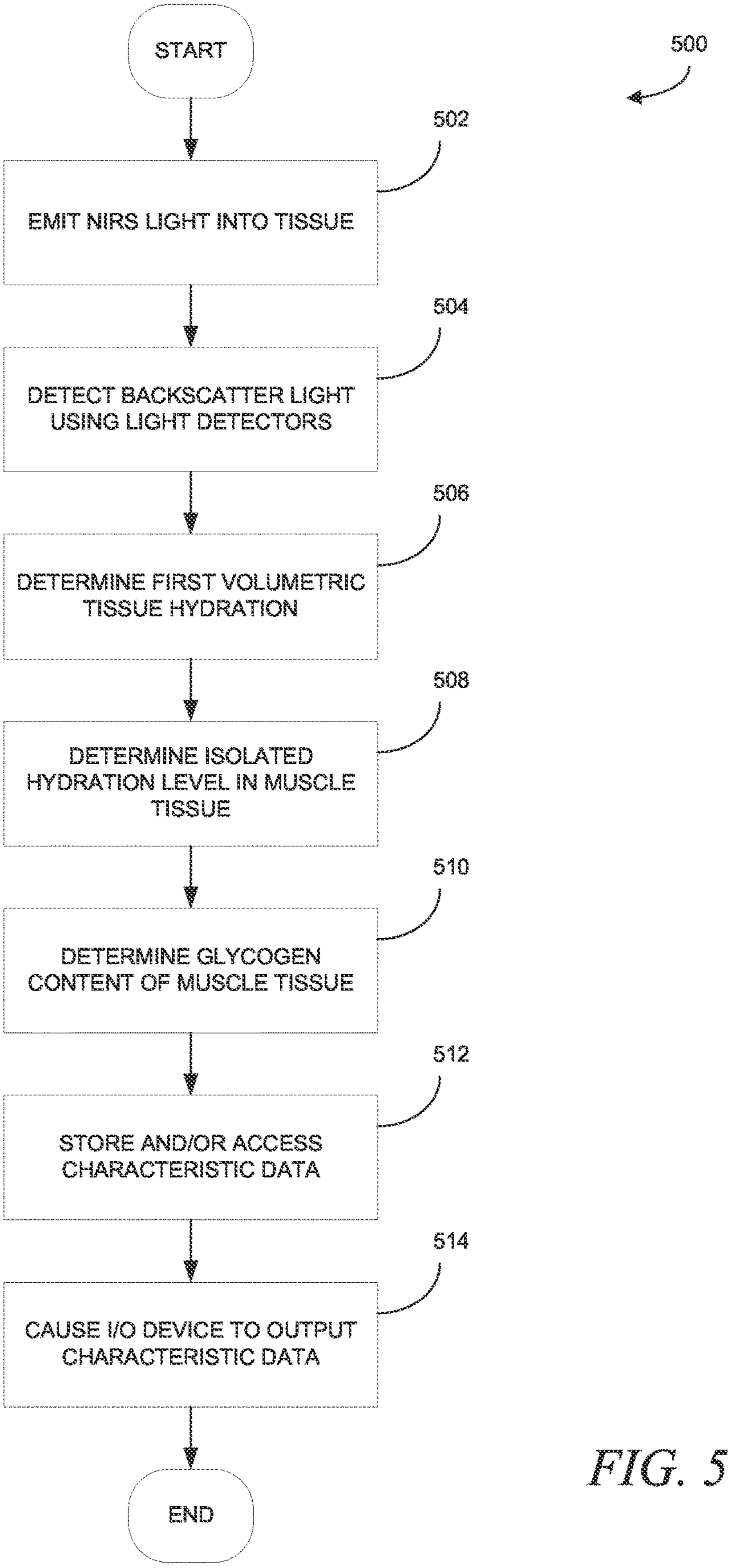
FIG. 5 is a flowchart for detecting a characteristic of muscle tissue in a muscle layer, in an example embodiment.

FIG. 5 is a flowchart 500 for detecting a characteristic of muscle tissue in a muscle layer 208, in an example embodiment. While the flowchart 500 is described with respect to the system 100, it is noted and emphasized that the flowchart may be implemented with respect to any suitable system or device.

At 502, the light emitter 102 emits NIRS light 210 into tissue 200.

At 504, the light detectors 104 detect backscatter light 212 from the light 210.

At 506, the processor 402 determines a first volumetric hydration level generally corresponding to the combination of the epidermis layer 202, the dermis layer 204, and the fat layer 206 based on the backscatter light 212 detected by the first light detector 104(1) as well as a second volumetric hydration level generally corresponding to the combination of the epidermis layer 202, the dermis layer 204, the fat layer 206, and the muscle layer 208.

At 508, the processor 402 determines an isolated hydration level in the muscle layer 208 by taking a difference between the first and second volumetric hydration levels.

At 510, the processor 402 determines a glycogen content or level of the muscle layer 208 based on the isolated hydration level of the muscle layer 208.

At 512, the processor 402 variously stores the data as determined at 506, 508, and/or 510 in the electronic data storage 408 and/or accesses data from the electronic data storage 408 for the determination of change in the characteristic over time or the comparison of the characteristic against a baseline, among other points of analysis.

At 514, the processor 402 causes the I/O device 406 to output data related to the characteristic, such as a hydration level, a glycogen level, or analytics related to the characteristic, including a time to recover from a current glycogen level and/or an available energy level.

Figure 6:
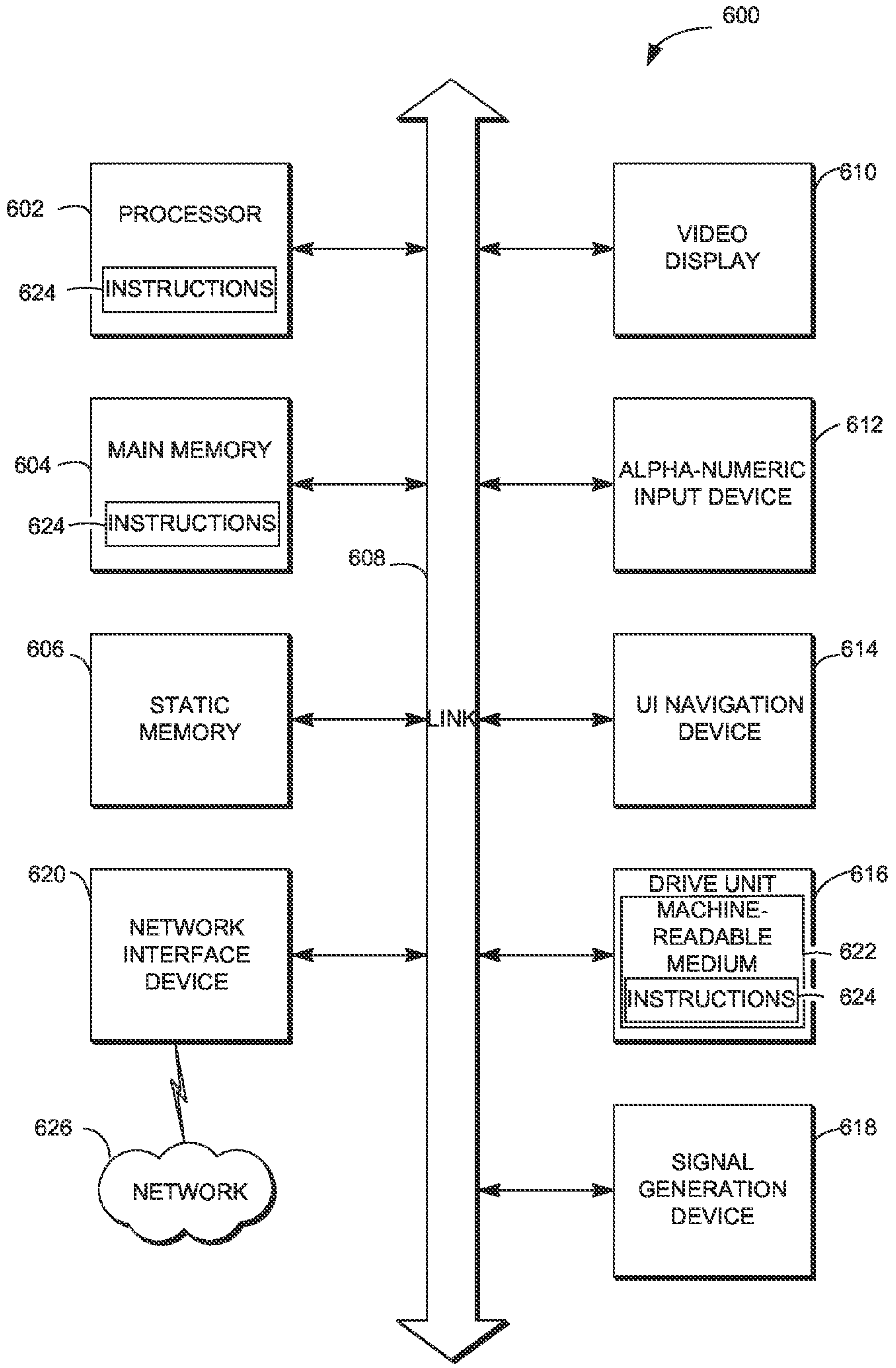
FIG. 6 is a block diagram illustrating components of a machine, according to some example embodiments, able to read instructions from a machine-readable medium.

FIG. 6 is a block diagram illustrating components of a machine 600, according to some example embodiments, able to read instructions from a machine-readable medium (e.g., a machine-readable storage medium) and perform any one or more of the methodologies discussed herein. Specifically, the machine 600 may implement the system 100 and/or wearable device 300 and the features included and described therein. The machine 600 thus describes specific hardware configurations on which the system 100 and/or wearable device 300 may be implemented and provided to users of the system 100 and/or wearable device 300.

FIG. 6 shows a diagrammatic representation of the machine 600 in the example form of a computer system and within which instructions 624 (e.g., software) for causing the machine 600 to perform any one or more of the methodologies discussed herein may be executed. In alternative embodiments, the machine 600 operates as a standalone device or may be connected (e.g., networked) to other machines. In a networked deployment, the machine 600 may operate in the capacity of a server machine or a client machine in a server-client network environment, or as a peer machine in a peer-to-peer (or distributed) network environment. The machine 600 may be a server computer, a client computer, a personal computer (PC), a tablet computer, a laptop computer, a netbook, a set-top box (STB), a personal digital assistant (PDA), a cellular telephone, a smartphone, a web appliance, a network router, a network switch, a network bridge, or any machine capable of executing the instructions 624, sequentially or otherwise, that specify actions to be taken by that machine. Further, while only a single machine is illustrated, the term "machine" shall also be taken to include a collection of machines that individually or jointly execute the instructions 624 to perform any one or more of the methodologies discussed herein.

The machine 600 includes a processor 602 (e.g., a central processing unit (CPU), a graphics processing unit (GPU), a digital signal processor (DSP), an application specific integrated circuit (ASIC), a radio-frequency integrated circuit (RFIC), or any suitable combination thereof), a main memory 604, and a static memory 606, which are configured to communicate with each other via a bus 608. The machine 600 may further include a graphics display 610 (e.g., a plasma display panel (PDP), a light emitting diode (LED) display, a liquid crystal display (LCD), a projector, or a cathode ray tube (CRT)). The machine 600 may also include an alphanumeric input device 612 (e.g., a keyboard), a cursor control device 614 (e.g., a mouse, a touchpad, a trackball, a joystick, a motion sensor, or other pointing instrument), a storage unit 616, a signal generation device 618 (e.g., a speaker), and a network interface device 620.

The storage unit 616 includes a machine-readable medium 622 on which is stored the instructions 624 (e.g., software) embodying any one or more of the methodologies or functions described herein. The instructions 624 may also reside, completely or at least partially, within the main memory 604, within the processor 602 (e.g., within the processor's cache memory), or both, during execution thereof by the machine 600. Accordingly, the main memory 604 and the processor 602 may be considered as machine-readable media. The instructions 624 may be transmitted or received over a network 626 via the network interface device 620.

Figure 7:
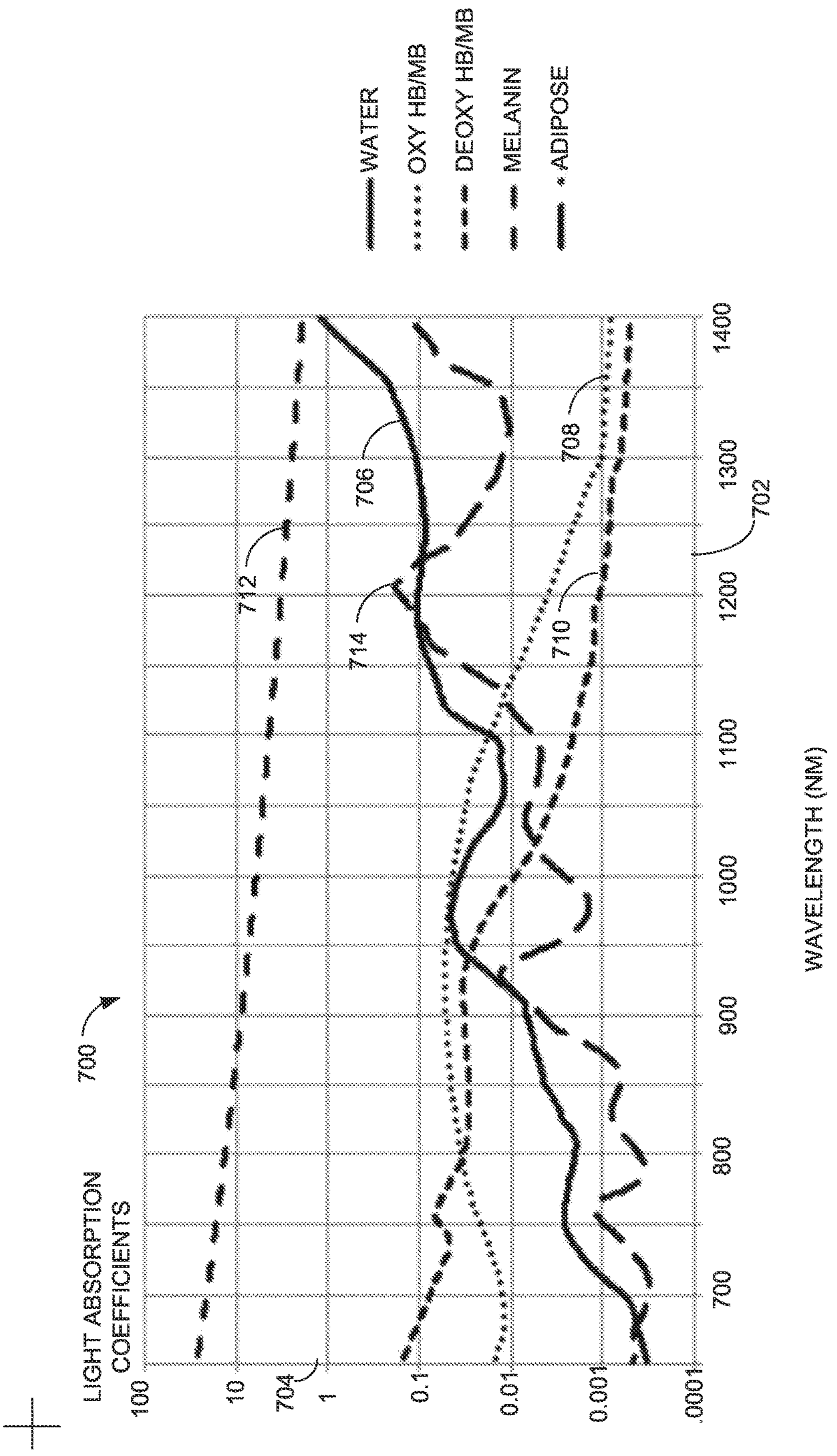
FIG. 7 is a graph depicting the absorption coefficients of various tissue parameters, in an example embodiment.

FIG. 7 is a graph 700 depicting the absorption coefficients of various tissue parameters, in an example embodiment. The graph 700 includes wavelengths on the x-axis 702 and light absorption coefficients on the y-axis 704. By considering the water curve 706, the oxygenated hemoglobin curve 708, the deoxygenated hemoglobin curve 710, the melanin curve 712, and the adipose curve 714, the six wavelengths emitted by the light emitter 102, i.e., 680 nanometers, 800 nanometers, 930 nanometers, 970 nanometers, 1210 nanometers, and 1310 nanometers, were selected.

In particular, for example, the 680 and 800 nm wavelengths are useful for creating sensitivity to total hemoglobin and hemoglobin saturation. Oxygenated and deoxygenated hemoglobin have essentially the same absorption coefficients at 800 nm, but substantially different absorption coefficients at 680 nanometers. Additionally, from 680 nanometers to 800 nanometers the water and fat absorbance is relatively low so the absorbance features of the hemoglobin dominate.

At 930 nanometers and 970 nanometers, water and oxygenated hemoglobin similarly coincide, with the hemoglobin absorbance is still relatively high. As a result, the 930 nanometer and 970 nanometer wavelengths may, in certain circumstances, tend to be applicable at relatively shallow depths D of the tissue 200. At 1210 nanometers and 1310 nanometers, the fat and water absorbance generally diverge. At such wavelengths, the fat and water absorbance is relatively higher than in the shorter wavelength range, providing the capacity to obtain information from greater depths D of the tissue 200.

The difference in absorption coefficients between 930 nanometers and 1210 nanometers may also be relatively significant. The oxygenated and deoxygenated hemoglobin absorption coefficients drop precipitously from 930 nanometers to 1210 nanometers while water and fat rise significantly. These varying shift may allow for differentiation between hemoglobin and water/fat.

The differences in the absorption coefficients provide for a system of equations to differentiate the amount of each tissue parameter, e.g., each chromophore. However, the various combinations of wavelengths and light detectors 104 in ratios that maximize sensitivity to the desired tissue parameters while minimizing sensitivity to confounding factors may be in the billions or even trillions of potential combinations. By analyzing the graph 700 desired combinations of light detectors 104 and wavelengths in ratios may provide for adequate sensitivity to water content of the muscle tissue 208 and, by extension, glycogen levels in the muscle tissue.

In an example, the system 100 utilizes five input ratios for the system of equations to solve for water content of the muscle tissue 208. Those ratios are:

Ratio 1=((third light detector 104(3) @ 930 nanometers)/(first light detector 104(1) @ 930 nanometers))/((third light detector 104(3) @ 970 nanometers)/(first light detector 104(1) @ 970 nanometers))

Ratio 2=((third light detector 104(3) @ 1310 nanometers)/(first light detector 104(1) @ 1310 nanometers))/((third light detector 104(3) @ 1210 nanometers)/(first light detector 104(1) @ 1210 nanometers))

Ratio 3=((first light detector 104(1) @ 680 nanometers)/(second light detector 104(2) @ 680 nanometers))/((first light detector 104(1) @ 800 nanometers)/(second light detector 104(2) @ 800 nanometers))

Ratio 4=((first light detector 104(1) @ 930 nanometers)/(second light detector 104(2) @ 930 nanometers))/((first light detector 104(1) @ 970 nanometers)/(second light detector 104(2) @ 970 nanometers))

Ratio 5=((first light detector 104(1) @ 1310 nanometers)/(second light detector 104(2) @ 1310 nanometers))/((first light detector 104(1) @ 1210 nanometers)/(second light detector 104(2) @ 1210 nanometers))

The ratios may then be utilized to determine water content and, by extension, glycogen levels of the muscle tissue 208, as disclosed in the '830 patent. In an example, the ratios may be applied to a process implemented by the following pseudocode which may correspond to steps 3 and 4 disclosed in the '830 patent. In various examples, the processes disclosed herein compare the ratios to look-up table ratios to identify a closest one of the look-up table ratios to the ratios as determined, each look-up table ratio corresponding to a predetermined glycogen level, the predetermined glycogen level of the closest one of the look-up table ratios being the glycogen level of the muscle tissue. In an example, the closest one of the look-up table ratios is identified based on a least-squares mechanism.

```
clc
clear
global S MU_WTR E_HBO2 E_HB MU_MEL MU_ADP
global LE_SK LD_SK LA_SK LM_SK LE_SH LD_SH LA_SH LM_SH LE_LG LD_LG LA_LG LM_LG
global F_MEL_D BHC F_WAT_A F_BLOOD_A
global ADP F_MEL_E F_WAT_SKIN THB_SKIN STO2_SKIN F_WAT_M THB_M SMO2_M
global J0
light_profile = 'C:\xxxxx.csv';
fid = fopen(light_profile);
temp = csvread(light_profile);
```

```
lambda_list = temp(:,1);
J0=temp(:,2:size(temp,2));
fclose(fid);
% Scalar Constants
F_MEL_D = 0.001;    %0.001
BHC = 150;          %150
F_WAT_A = 0.10;     %0.10
F_BLOOD_A = 0.0025; %0.0025
% Load Constant functions of Wavelength
fid = fopen(strcat('C:\xxxxx.dat'));
C = textscan(fid, '%f %f %f %f %f %f %f');
fclose(fid);
if lambda_list ~= C{1};
   error('Light Profile and Properties do not match');
end
S = C{2};
MU_WTR = C{3};
E_HBO2 = C{4};
E_HB = C{5};
MU_MEL = C{6};
MU_ADP = C{7};
datapath='xxxxx;
count=0;
index=zeros(1,5);
tissuevals=zeros(1,5);
```

```
sensorvals=zeros(1,5);

layerlist = {'1_5', '1_8', '2_1', '2_4', '2_7', '3_0', '3_3', '3_6', '4_0', '4_5',
'5_0', '5_7', '6_5', '7_2', '8_0', '9_0', '10_0', '11_0', '12_0', '13_5', '15_0'};

ADPlist = [1.5, 1.8, 2.1, 2.4, 2.7, 3.0, 3.3, 3.6, 4.0, 4.5, 5.0, 5.7, 6.5,
7.2, 8.0, 9.0, 10.0, 11.0, 12.0, 13.5, 15.0];

for adp_i=1:21

  laysym = layerlist{adp_i};

  ADP = ADPlist(adp_i);

    %Load the pathlength data based on the adipose thickness

  lambda_scat_list = 600:20:1400; % modeling was done from 600 to
1400 nm in 20 nm increments

    LE_SK_coarse = (importdata(strcat(datapath,
laysym,'\6_25_E_PL_',laysym,'.txt')))';

  LD_SK_coarse = (importdata(strcat(datapath,
laysym,'\6_25_D_PL_',laysym,'.txt')))';

  LA_SK_coarse = (importdata(strcat(datapath,
laysym,'\6_25_A_PL_',laysym,'.txt')))';

  LM_SK_coarse = (importdata(strcat(datapath,
laysym,'\6_25_M_PL_',laysym,'.txt')))';

  nrays = size(LE_SK_coarse,2);

  LE_SK=zeros(size(lambda_list,1),nrays);

  LD_SK=zeros(size(lambda_list,1),nrays);

  LA_SK=zeros(size(lambda_list,1),nrays);

  LM_SK=zeros(size(lambda_list,1),nrays);

  for i_lambda = 1:size(lambda_list,1);

    lambda = lambda_list(i_lambda);
```

```
for i_scat = 1:size(lambda_scat_list,2)-1
    if lambda > lambda_scat_list(i_scat) && lambda <=
lambda_scat_list(i_scat+1)
        nray_lo = fix((lambda_scat_list(i_scat+1) -
lambda)/(lambda_scat_list(i_scat+1)-lambda_scat_list(i_scat))*nrays);
        nray_hi = nrays - nray_lo;
        LE_SK(i_lambda,1:nray_lo) = LE_SK_coarse(i_scat,nrays-
nray_lo+1:nrays);
        LD_SK(i_lambda,1:nray_lo) = LD_SK_coarse(i_scat,nrays-
nray_lo+1:nrays);
        LA_SK(i_lambda,1:nray_lo) = LA_SK_coarse(i_scat,nrays-
nray_lo+1:nrays);
        LM_SK(i_lambda,1:nray_lo) = LM_SK_coarse(i_scat,nrays-
nray_lo+1:nrays);
        LE_SK(i_lambda,nray_lo+1:nrays) =
LE_SK_coarse(i_scat+1,1:nray_hi);
        LD_SK(i_lambda,nray_lo+1:nrays) =
LD_SK_coarse(i_scat+1,1:nray_hi);
        LA_SK(i_lambda,nray_lo+1:nrays) =
LA_SK_coarse(i_scat+1,1:nray_hi);
        LM_SK(i_lambda,nray_lo+1:nrays) =
LM_SK_coarse(i_scat+1,1:nray_hi);
    end
  end
end
clear LE_SK_coarse LD_SK_coarse LA_SK_coarse
LM_SK_coarse;
```

```
LE_SH_coarse = (importdata(strcat(datapath,
laysym,'\12_5_E_PL_',laysym,'.txt')))';
LD_SH_coarse = (importdata(strcat(datapath,
laysym,'\12_5_D_PL_',laysym,'.txt')))';
LA_SH_coarse = (importdata(strcat(datapath,
laysym,'\12_5_A_PL_',laysym,'.txt')))';
LM_SH_coarse = (importdata(strcat(datapath,
laysym,'\12_5_M_PL_',laysym,'.txt')))';
nrays = size(LE_SH_coarse,2);
LE_SH=zeros(size(lambda_list,1),nrays);
LD_SH=zeros(size(lambda_list,1),nrays);
LA_SH=zeros(size(lambda_list,1),nrays);
LM_SH=zeros(size(lambda_list,1),nrays);
for i_lambda = 1:size(lambda_list,1);
  lambda = lambda_list(i_lambda);
  for i_scat = 1:size(lambda_scat_list,2)-1
    if lambda > lambda_scat_list(i_scat) && lambda <=
lambda_scat_list(i_scat+1)
      nray_lo = fix((lambda_scat_list(i_scat+1) -
lambda)/(lambda_scat_list(i_scat+1)-lambda_scat_list(i_scat))*nrays);
      nray_hi = nrays - nray_lo;
      LE_SH(i_lambda,1:nray_lo) = LE_SH_coarse(i_scat,nrays-
nray_lo+1:nrays);
      LD_SH(i_lambda,1:nray_lo) = LD_SH_coarse(i_scat,nrays-
nray_lo+1:nrays);
      LA_SH(i_lambda,1:nray_lo) = LA_SH_coarse(i_scat,nrays-
nray_lo+1:nrays);
```

```
LM_SH(i_lambda,1:nray_lo) = LM_SH_coarse(i_scat,nrays-
nray_lo+1:nrays);
LE_SH(i_lambda,nray_lo+1:nrays) =
LE_SH_coarse(i_scat+1,1:nray_hi);
LD_SH(i_lambda,nray_lo+1:nrays) =
LD_SH_coarse(i_scat+1,1:nray_hi);
LA_SH(i_lambda,nray_lo+1:nrays) =
LA_SH_coarse(i_scat+1,1:nray_hi);
LM_SH(i_lambda,nray_lo+1:nrays) =
LM_SH_coarse(i_scat+1,1:nray_hi);
end
end
end
clear LE_SH_coarse LD_SH_coarse LA_SH_coarse
LM_SH_coarse;

LE_LG_coarse = (importdata(strcat(datapath,
laysym,'\25_E_PL_',laysym,'.txt')))';
LD_LG_coarse = (importdata(strcat(datapath,
laysym,'\25_D_PL_',laysym,'.txt')))';
LA_LG_coarse = (importdata(strcat(datapath,
laysym,'\25_A_PL_',laysym,'.txt')))';
LM_LG_coarse = (importdata(strcat(datapath,
laysym,'\25_M_PL_',laysym,'.txt')))';
nrays = size(LE_LG_coarse,2);
LE_LG=zeros(size(lambda_list,1),nrays);
LD_LG=zeros(size(lambda_list,1),nrays);
```

```
LA_LG=zeros(size(lambda_list,1),nrays);
LM_LG=zeros(size(lambda_list,1),nrays);
for i_lambda = 1:size(lambda_list,1);
    lambda = lambda_list(i_lambda);
    for i_scat = 1:size(lambda_scat_list,2)-1
        if lambda > lambda_scat_list(i_scat) && lambda <=
lambda_scat_list(i_scat+1)
            nray_lo = fix((lambda_scat_list(i_scat+1) -
lambda)/(lambda_scat_list(i_scat+1)-lambda_scat_list(i_scat))*nrays);
            nray_hi = nrays - nray_lo;
            LE_LG(i_lambda,1:nray_lo) = LE_LG_coarse(i_scat,nrays-
nray_lo+1:nrays);
            LD_LG(i_lambda,1:nray_lo) = LD_LG_coarse(i_scat,nrays-
nray_lo+1:nrays);
            LA_LG(i_lambda,1:nray_lo) = LA_LG_coarse(i_scat,nrays-
nray_lo+1:nrays);
            LM_LG(i_lambda,1:nray_lo) =
LM_LG_coarse(i_scat,nrays-nray_lo+1:nrays);
            LE_LG(i_lambda,nray_lo+1:nrays) =
LE_LG_coarse(i_scat+1,1:nray_hi);
            LD_LG(i_lambda,nray_lo+1:nrays) =
LD_LG_coarse(i_scat+1,1:nray_hi);
            LA_LG(i_lambda,nray_lo+1:nrays) =
LA_LG_coarse(i_scat+1,1:nray_hi);
            LM_LG(i_lambda,nray_lo+1:nrays) =
LM_LG_coarse(i_scat+1,1:nray_hi);
        end
```

```
  end
end
clear LE_LG_coarse LD_LG_coarse LA_LG_coarse
LM_LG_coarse;
  F_MEL_E = 0.02;
THB_SKIN = .4;
STO2_SKIN = 100;
fwatsk_i=0;
for F_WAT_SKIN = .60:.05:.70
  fwatsk_i=fwatsk_i+1;
  fwatm_i=0;
  for F_WAT_M =.65:.05:.75
    fwatm_i=fwatm_i+1;
    thbm_i=0;
    for THB_M = 11:1:13
      fprintf('%i \n',count);
      thbm_i=thbm_i+1;
      smo2m_i=0;
      for SMO2_M = 0:20:100
        smo2m_i=smo2m_i+1;
        count=count+1;
        index(count,:) = [adp_i, fwatsk_i, fwatm_i, thbm_i,
smo2m_i];
        tissuevals(count,:)=[ADP, F_WAT_SKIN, F_WAT_M,
THB_M, SMO2_M];
```

```
            J=Equations();
            sensorvals(count,1) = (J(3)/J(9))/(J(4)/J(10));
            sensorvals(count,2) = (J(6)/J(12))/(J(5)/J(11));
            sensorvals(count,3) = (J(7)/J(13))/(J(8)/J(14));
            sensorvals(count,4) = (J(9)/J(15))/(J(10)/J(16));
            sensorvals(count,5) = (J(12)/J(18))/(J(11)/J(17));
          end
        end
      end
    end
  end
  fid = fopen('sensorvals.dat','w');
  ncols=size(index,2) + size(tissuevals,2) + size(sensorvals,2);
  fformat = char(strcat(repmat('%d ',1,size(index,2)),{' '},repmat('%.4f
',1,size(tissuevals,2)),{' '},repmat('%.4f ',1,size(sensorvals,2)),'\n'));
  for row = 1:count
    fprintf(fid,fformat,index(row,:),tissuevals(row,:),sensorvals(row,:));
  end
  fclose('all');
  clc
  clear
  ndims = 5;
  nlambda = 6;
  fformat = char(strcat(repmat('%d ',1,ndims),{' '},repmat('%.20f
',1,ndims),{' '},repmat('%.20f ',1,ndims),'\n'));
```

```
fid =
fopen(strcat('C:\Users\Rog\Fortiori\Matlab\Glycogen5b','\sensorvals.dat'));
        LITVSV = textscan(fid, fformat);
        fclose(fid);
        %ix = zeros(numel(LITVSV{1}),size(dimarray,2));
        lutv = zeros(1,ndims);
        lusv = zeros(1,ndims);
        ix = zeros(numel(LITVSV{1}),ndims);
        LUTV =
cell(max(LITVSV{1}(:)),max(LITVSV{2}(:)),max(LITVSV{3}(:)),max(LITVSV{
4}(:)),max(LITVSV{5}(:)));
        LUSV =
cell(max(LITVSV{1}(:)),max(LITVSV{2}(:)),max(LITVSV{3}(:)),max(LITVSV{
4}(:)),max(LITVSV{5}(:)));
        for count = 1:numel(LITVSV{1})
            for dim = 1:ndims
              ix(count,dim) = LITVSV{dim}(count);
              lutv(dim) = LITVSV{ndims+dim}(count);
              lusv(dim) = LITVSV{2*ndims + dim}(count);
            end
            LUTV{ix(count,1), ix(count,2), ix(count,3), ix(count,4),
ix(count,5)} = lutv;
            LUSV{ix(count,1), ix(count,2), ix(count,3), ix(count,4),
ix(count,5)} = lusv;
        end
        TESTSV{1} = [0.9379, 0.8266, 2.1383, 0.7494, 1.1336];
```

```
TESTSV{2} = [0.9379, 0.8266, 2.1383, 0.7494, 1.1236];
TESTSV{3} = [0.9379, 0.8266, 2.1383, 0.7494, 1.1136];
TESTSV{4} = [0.9379, 0.8266, 2.1383, 0.7494, 1.1036];
% fformat = char(strcat(repmat('%.4f ',1,ndims),{' '},repmat('%.4f
',1,nspace*nlambda),'\n'));
% fid = fopen(strcat('C:\yyyyy.dat'));
% TITVSV = textscan(fid, fformat);
% fclose(fid);
%
% testtv = zeros(1,size(dimarray,2));
% TESTTV = cell(1,numel(TITVSV{1}));
% TESTSV = cell(1,numel(TITVSV{1}));
%
% for count = 1:numel(TITVSV{1})
%     for dim = 1:size(dimarray,2)
%         testtv(dim) = TITVSV{dimarray(dim)}(count);
%     end
%     for lambda = 1:nlambda
%         short(lambda) = TITVSV{ndims + lambda}(count);
%         medium(lambda) = TITVSV{ndims + nlambda +
lambda}(count);
%         long(lambda) = TITVSV{ndims + 2*nlambda +
lambda}(count);
%     end
```

```
% testsv =
Ratios(third_light_detector,first_light_detector,second_light_detector,alg);
%
% TESTTV{count} = testtv;
% TESTSV{count} = testsv;
% end
CALCTV = cell(1,size(TESTSV,2));
ERROR = cell(1,size(TESTSV,2));
CL = zeros(1,size(TESTSV,2));
for test = 1:size(TESTSV,2);
  %find the closest value
  SUMSQ = 9999;
  for count = 1:size(ix,1)
    sumsq = 0;
    closest = 0;
    for dim = 1:ndims
      lusv = LUSV{ix(count,1), ix(count,2), ix(count,3), ix(count,4),
ix(count,5)}(dim);
      sumsq = sumsq + ((TESTSV{test}(dim) -
lusv)/(TESTSV{test}(dim) + lusv))^2;
    end
    if sumsq < SUMSQ
      SUMSQ = sumsq;
      cl = count;
    end
```

```
end
   low = zeros(ndims);
high = zeros(ndims);
   %calculate the derivatives
for dim = 1:ndims
   if ix(cl,dim) == 1
      low(dim) = 1;
   else
      low(dim) = ix(cl,dim) - 1;
   end
   if ix(cl,dim) == max(ix(:,dim))
      high(dim) = max(ix(:,dim));
   else
      high(dim) = ix(cl,dim) + 1;
   end
end
 dTV(1) = LUTV{high(1), ix(cl,2), ix(cl,3), ix(cl,4), ix(cl,5)}(1) -
LUTV{low(1), ix(cl,2), ix(cl,3), ix(cl,4), ix(cl,5)}(1);
dTV(2) = LUTV{ix(cl,1), high(2), ix(cl,3), ix(cl,4), ix(cl,5)}(2) -
LUTV{ix(cl,1), low(2), ix(cl,3), ix(cl,4), ix(cl,5)}(2);
dTV(3) = LUTV{ix(cl,1), ix(cl,2), high(3), ix(cl,4), ix(cl,5)}(3) -
LUTV{ix(cl,1), ix(cl,2), low(3), ix(cl,4), ix(cl,5)}(3);
dTV(4) = LUTV{ix(cl,1), ix(cl,2), ix(cl,3), high(4), ix(cl,5)}(4) -
LUTV{ix(cl,1), ix(cl,2), ix(cl,3), low(4), ix(cl,5)}(4);
dTV(5) = LUTV{ix(cl,1), ix(cl,2), ix(cl,3), ix(cl,4), high(5)}(5) -
LUTV{ix(cl,1), ix(cl,2), ix(cl,3), ix(cl,4), low(5)}(5);
```

```
Jac=zeros(ndims,ndims);
for i = 1:ndims
    Jac(i,1) = (LUSV{high(1), ix(cl,2), ix(cl,3), ix(cl,4), ix(cl,5)}(i) - LUSV{low(1), ix(cl,2), ix(cl,3), ix(cl,4), ix(cl,5)}(i))/dTV(1);
    Jac(i,2) = (LUSV{ix(cl,1), high(2), ix(cl,3), ix(cl,4), ix(cl,5)}(i) - LUSV{ix(cl,1), low(2), ix(cl,3), ix(cl,4), ix(cl,5)}(i))/dTV(2);
    Jac(i,3) = (LUSV{ix(cl,1), ix(cl,2), high(3), ix(cl,4), ix(cl,5)}(i) - LUSV{ix(cl,1), ix(cl,2), low(3), ix(cl,4), ix(cl,5)}(i))/dTV(3);
    Jac(i,4) = (LUSV{ix(cl,1), ix(cl,2), ix(cl,3), high(4), ix(cl,5)}(i) - LUSV{ix(cl,1), ix(cl,2), ix(cl,3), low(4), ix(cl,5)}(i))/dTV(4);
    Jac(i,5) = (LUSV{ix(cl,1), ix(cl,2), ix(cl,3), ix(cl,4), high(5)}(i) - LUSV{ix(cl,1), ix(cl,2), ix(cl,3), ix(cl,4), low(5)}(i))/dTV(5);
end
    DeltSV = LUSV{ix(cl,1), ix(cl,2), ix(cl,3), ix(cl,4), ix(cl,5)}(:) - TESTSV{test}(:);
    DeltTV = Jac\DeltSV;
    CALCTV{test} = LUTV{ix(cl,1), ix(cl,2), ix(cl,3), ix(cl,4), ix(cl,5)}(:) - DeltTV(:);
CL(test) = cl;
%ERROR{test} = CALCTV{test}(:) - TESTTV{test}(:);
end
for i = 1:size(TESTSV,2);
    temp(i,:) = CALCTV{i}(:);
    %temp2(i,:) = TESTTV{i}(:);
end
```

Figure 8:
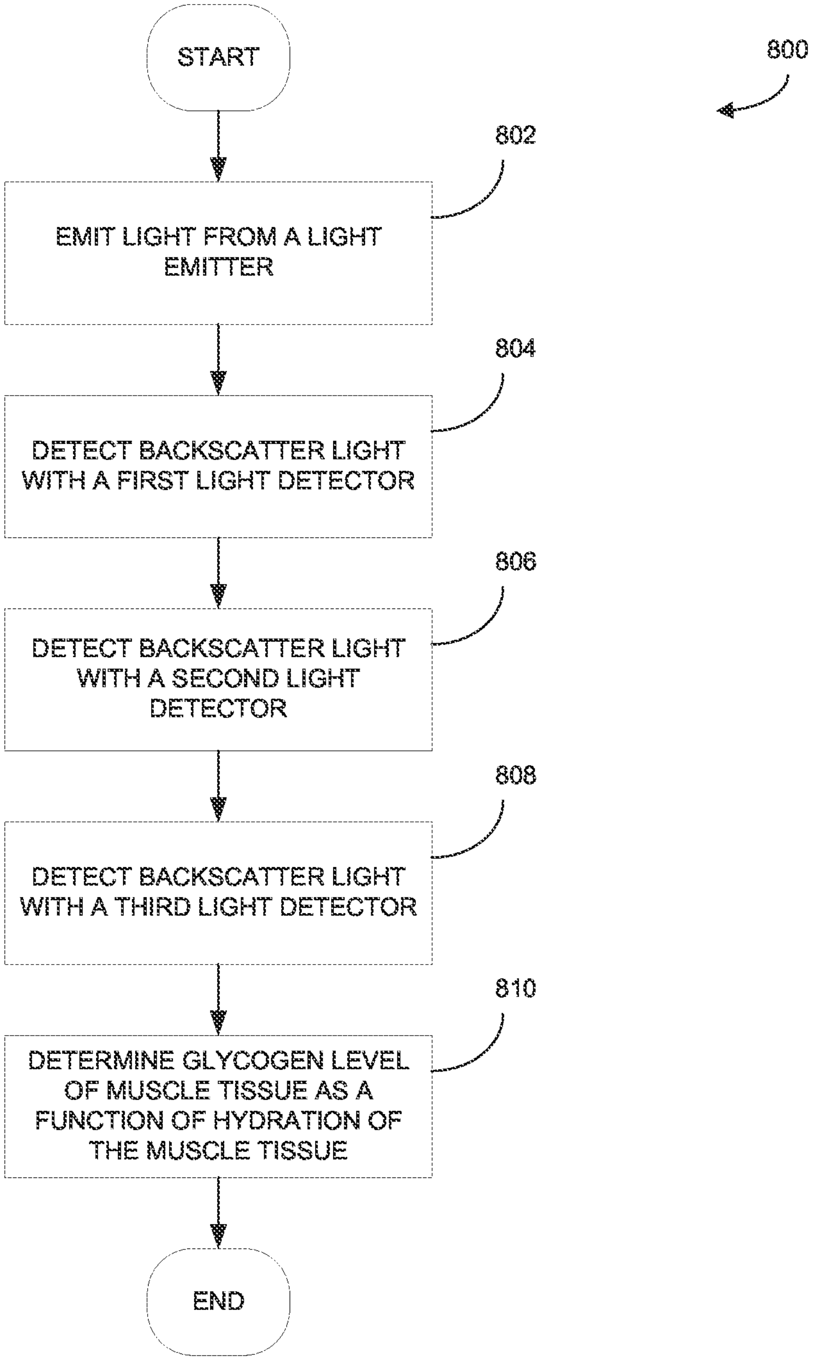
FIG. 8 is a flowchart for determining a glycogen level of muscle tissue in a muscle layer, in an example embodiment.

FIG. 8 is a flowchart 800 for determining a glycogen level of muscle tissue in a muscle layer 208, in an example embodiment. May be implemented with to the system 100 or with any suitable system or device.

At 802, light is emitted from a light emitter at a first wavelength over a range of approximately 900 to 1000 nanometers and at a second wavelength over a range of approximately 1300 to 1400 nanometers. In an example, the light emitter comprises a first light emitting diode (LED) configured to emit light at the first wavelength and a second LED configured to emit light at the second wavelength. In an example, the light emitter emits light at wavelengths between approximately 660 and approximately 820 nanometers. In an example, the light emitter comprises a first light emitting diode (LED) emitting light at the first wavelength, a second LED emitting light at the second wavelength, and four LEDs emitting the light between approximately 660 and approximately 820 nanometers. In an example, the first wavelength is approximately 970 nanometers and the second wavelength is approximately 1,310 nanometers. In an example, emitting the light from the light emitter further comprises emitting light at a third wavelength, a fourth wavelength, a fifth wavelength, and a sixth wavelength. In an example, the third wavelength is approximately 680 nanometers, the fourth wavelength is approximately 800 nanometers, the fifth wavelength is approximately 970 nanometers, and the sixth wavelength is approximately 1210 nanometers.

At 804, backscatter light from non-muscle tissue is detected with a first light detector spaced at a first distance from the light emitter.

At 806, backscatter light is detected with a second light detector spaced at a second distance from the light emitter from non-muscle tissue and from muscle tissue, the second distance approximately twice the first distance. In an example, the first distance is approximately 12.5 millimeters and the second distance is approximately 25 millimeters. In an example, at least one of the first light detector and the second light detector detects backscatter light from the light between approximately 660 and approximately 820 nanometers. In an example, an oxygen level of hemoglobin in blood is determinable based on the backscatter light from the light between approximately 660 and approximately 820 nanometers. In an example, the first and second light detectors are photodiodes. In an example, the light emitter and first and second light detectors are positioned on a wearable device configured to be positioned on and secured to a forearm of a user proximate an elbow of the user.

At 808, detecting, with a third light detector spaced between the light emitter and the first light detector, backscatter light from the light emitter.

At 810, a glycogen level of muscle tissue is determined by a processor as a function of hydration of the muscle tissue based on a relationship between backscatter light from the muscle tissue as detected by the second light detector and backscatter light from non-muscle tissue as detected by the first light detector. In an example, the relationship is a differential relationship between the backscatter light detected by the second light detector and the backscatter light detected by the first light detector. In an example, the muscle tissue is in a muscle layer below layers of non-muscle tissue, the muscle layer having a depth from a skin surface, and wherein the second distance is approximately twice the depth of the muscle layer from the skin surface. In an example, the light emitter and the first and second light detectors are components of a wearable device and the processor is a component of an external device different than the wearable device. In an example, determining the glycogen level of the muscle tissue is as the function of hydration of the muscle tissue based on a relationship between backscatter light from the muscle tissue and the non-muscle tissue as detected by the first, second, and third light detectors. In an alternative example, the processor determines the glycogen level by determining ratios including backscatter light detected by the first light detector and the second light detector at at least one of the first wavelength and the second wavelength and comparing the ratios to look-up table ratios to identify a closest one of the look-up table ratios to the ratios as determined, each look-up table ratio corresponding to a predetermined glycogen level, the predetermined glycogen level of the closest one of the look-up table ratios being the glycogen level of the muscle tissue.

EXAMPLES

In Example 1, a system includes a light emitter configured to emit light at a first wavelength over a range of approximately 900 to 1000 nanometers and at a second wavelength over a range of approximately 1300 to 1400 nanometers, a first light detector spaced at a first distance from the light emitter, and a second light detector spaced at a second distance from the light emitter, the second distance approximately twice the first distance, and a processor configured to determine a glycogen level of muscle tissue as a function of hydration of the muscle tissue based on a relationship between backscatter light from the muscle tissue as detected by the second light detector and backscatter light from non-muscle tissue as detected by the first light detector.

In Example 2, the system of Example 1 optionally further includes that the processor is configured to determine the relationship based on a differential relationship between the backscatter light detected by the second light detector and the backscatter light detected by the first light detector.

In Example 3, the system of any one or more of Examples 1 and 2 optionally further includes that the muscle tissue is in a muscle layer below layers of non-muscle tissue, the muscle layer having a depth from a skin surface, and wherein the second distance is approximately twice the depth of the muscle layer from the skin surface.

In Example 4, the system of any one or more of Examples 1-3 optionally further includes that the first distance is approximately 12.5 millimeters and the second distance is approximately 25 millimeters.

In Example 5, the system of any one or more of Examples 1-4 optionally further includes that the light emitter comprises a first light emitting diode (LED) configured to emit light at the first wavelength and a second LED configured to emit light at the second wavelength.

In Example 6, the system of any one or more of Examples 1-5 optionally further includes that the light emitter is further configured to emit light at wavelengths between approximately 660 and approximately 820 nanometers, at least one of the first light detector and the second light detector is configured to detect backscatter light from the light between approximately 660 and approximately 820 nanometers, wherein the processor is configured to determine an oxygen level of hemoglobin in blood based on the backscatter light from the light between approximately 660 and approximately 820 nanometers.

In Example 7, the system of any one or more of Examples 1-6 optionally further includes that the light emitter comprises a first light emitting diode (LED) configured to emit light at the first wavelength, a second LED configured to emit light at the second wavelength, and four LEDs configured to emit the light between approximately 660 and approximately 820 nanometers.

In Example 8, the system of any one or more of Examples 1-7 optionally further includes that the first and second light detectors are photodiodes.

In Example 9, the system of any one or more of Examples 1-8 optionally further includes that the light emitter and first and second light detectors are positioned on a wearable device configured to be positioned on and secured to a forearm of a user proximate an elbow of the user.

In Example 10, the system of any one or more of Examples 1-9 optionally further includes a processor, communicatively coupled to the light emitter and the first and second light detectors, configured to determine the glycogen level of the muscle tissue and cause a user interface to display information related to the glycogen level of the muscle tissue.

In Example 11, the system of any one or more of Examples 1-10 optionally further includes that the light emitter and the first and second light detectors are components of a wearable device and the processor is a component of an external device different than the wearable device.

In Example 12, the system of any one or more of Examples 1-11 optionally further includes that the light emitter, the first and second light detectors, and the processor are components of a wearable device.

In Example 13, the system of any one or more of Examples 1-12 optionally further includes that the first wavelength is approximately 970 nanometers and the second wavelength is approximately 1310 nanometers.

In Example 14, the system of any one or more of Examples 1-13 optionally further includes that the light emitter is further configured to emit light at a third wavelength, a fourth wavelength, a fifth wavelength, and a sixth wavelength, and further comprising a third light detector spaced between the light emitter and the first light detector and wherein the processor is configured to determine the glycogen level of the muscle tissue as the function of hydration of the muscle tissue based on a relationship between backscatter light from the muscle tissue and the non-muscle tissue as detected by the first, second, and third light detectors.

In Example 15, the system of any one or more of Examples 1-14 optionally further includes that the third wavelength is approximately 680 nanometers, the fourth wavelength is approximately 800 nanometers, the fifth wavelength is approximately 970 nanometers, and the sixth wavelength is approximately 1210 nanometers.

In Example 16, a wearable device includes a light emitter configured to emit light at a first wavelength over a range of approximately 900 to 1000 nanometers and at a second wavelength over a range of approximately 1300 to 1400 nanometers, a first light detector spaced at a first distance from the light emitter, a second light detector spaced at a second distance from the light emitter, the second distance approximately twice the first distance, and a processor configured to determine a glycogen level of muscle tissue as a function of hydration of the muscle tissue based on a relationship between backscatter light from the muscle tissue as detected by the second light detector and backscatter light from non-muscle tissue as detected by the first light detector.

In Example 17, the wearable device of Example 16 optionally further includes that the relationship is a differential relationship between the backscatter light detected by the second light detector and the backscatter light detected by the first light detector.

In Example 18, the wearable device of any one or more of Examples 16 and 17 optionally further includes that the muscle tissue is in a muscle layer below layers of non-muscle tissue, the muscle layer having a depth from a skin surface, and wherein the second distance is approximately twice the depth of the muscle layer from the skin surface.

In Example 19, the wearable device of any one or more of Examples 16-18 optionally further includes that the first distance is approximately 12.5 millimeters and the second distance is approximately 25 millimeters.

In Example 20, the wearable device of any one or more of Examples 16-19 optionally further includes that the light emitter comprises a first light emitting diode (LED) configured to emit light at the first wavelength and a second LED configured to emit light at the second wavelength.

In Example 21, the wearable device of any one or more of Examples 16-20 optionally further includes that the light emitter is further configured to emit light at wavelengths between approximately 660 and approximately 820 nanometers, wherein at least one of the first light detector and the second light detector is configured to detect backscatter light from the light between approximately 660 and approximately 820 nanometers, and wherein the processor is further configured to determine an oxygen level of hemoglobin in blood based on the backscatter light from the light between approximately 660 and approximately 820 nanometers.

In Example 22, the wearable device of any one or more of Examples 16-21 optionally further includes that the light emitter comprises a first light emitting diode (LED) configured to emit light at the first wavelength, a second LED configured to emit light at the second wavelength, and four LEDs configured to emit the light between approximately 660 and approximately 820 nanometers.

In Example 23, the wearable device of any one or more of Examples 16-22 optionally further includes that the first and second light detectors are photodiodes.

In Example 24, the wearable device of any one or more of Examples 16-23 optionally further includes that the light emitter and first and second light detectors are positioned on a wearable device configured to be positioned on and secured to a forearm of a user proximate an elbow of the user.

In Example 25, the wearable device of any one or more of Examples 16-24 optionally further includes the processor is further configured to cause a user interface to display information related to the glycogen level of the muscle tissue.

In Example 26, the wearable device of any one or more of Examples 16-25 optionally further includes that the first wavelength is approximately 970 nanometers and the second wavelength is approximately 1310 nanometers.

In Example 27, the wearable device of any one or more of Examples 16-26 optionally further includes that the light emitter is further configured to emit light at a third wavelength, a fourth wavelength, a fifth wavelength, and a sixth wavelength, and further comprising a third light detector spaced between the light emitter and the first light detector, wherein the processor is configured to determine the glycogen level of the muscle tissue as the function of hydration of the muscle tissue based on a relationship between backscatter light from the muscle tissue and the non-muscle tissue as detected by the first, second, and third light detectors.

In Example 28, the wearable device of any one or more of Examples 16-27 optionally further includes that the third wavelength is approximately 680 nanometers, the fourth wavelength is approximately 800 nanometers, the fifth wavelength is approximately 970 nanometers, and the sixth wavelength is approximately 1210 nanometers.

In Example 29, a method includes emitting, from a light emitter, light at a first wavelength over a range of approximately 900 to 1000 nanometers and at a second wavelength over a range of approximately 1300 to 1400 nanometers, detecting, with a first light detector spaced at a first distance from the light emitter, backscatter light from non-muscle tissue, detecting, with a second light detector spaced at a second distance from the light emitter, backscatter light from non-muscle tissue and from muscle tissue, the second distance approximately twice the first distance, and determining, with a processor, a glycogen level of muscle tissue as a function of hydration of the muscle tissue based on a relationship between backscatter light from the muscle tissue as detected by the second light detector and backscatter light from non-muscle tissue as detected by the first light detector.

In Example 30, the method of Example 29 optionally further includes that determining the glycogen level includes determining the hydration based on the relationship being a differential relationship between the backscatter light detected by the second light detector and the backscatter light detected by the first light detector.

In Example 31, the method of any one or more of Examples 29 and 30 optionally further includes that the muscle tissue is in a muscle layer below layers of non-muscle tissue, the muscle layer having a depth from a skin surface, and wherein detecting the backscatter light includes detecting the backscatter light at a second distance approximately twice the depth of the muscle layer from the skin surface.

In Example 32, the method of any one or more of Examples 29-31 optionally further includes that the first distance is approximately 12.5 millimeters and the second distance is approximately 25 millimeters.

In Example 33, the method of any one or more of Examples 29-32 optionally further includes that emitting light comprises emitting light from a first light emitting diode (LED) configured to emit light at the first wavelength and emitting light from a second LED configured to emit light at the second wavelength.

In Example 34, the method of any one or more of Examples 29-33 optionally further includes that emitting light comprises emitting light at wavelengths between approximately 660 and approximately 820 nanometers, wherein at least one of the first light detector and the second light detector detects backscatter light from the light between approximately 660 and approximately 820 nanometers, and further comprising determining, with the processor, an oxygen level of hemoglobin in blood is based on the backscatter light from the light between approximately 660 and approximately 820 nanometers.

In Example 35, the method of any one or more of Examples 29-34 optionally further includes that emitting light comprises emitting light from a first light emitting diode (LED) at the first wavelength, emitting light from a second LED at the second wavelength, and emitting light from four LEDs between approximately 660 and approximately 820 nanometers.

In Example 36, the method of any one or more of Examples 29-35 optionally further includes that the first wavelength is approximately 970 nanometers and the second wavelength is approximately 1,310 nanometers.

In Example 37, the method of any one or more of Examples 29-36 optionally further includes that wherein emitting the light from the light emitter further comprises emitting light at a third wavelength, a fourth wavelength, a fifth wavelength, and a sixth wavelength, and further comprising detecting, with a third light detector spaced between the light emitter and the first light detector, backscatter light from the light emitter, wherein determining the glycogen level of the muscle tissue is as the function of hydration of the muscle tissue based on a relationship between backscatter light from the muscle tissue and the non-muscle tissue as detected by the first, second, and third light detectors.

In Example 38, the method of any one or more of Examples 29-37 optionally further includes that the third wavelength is approximately 680 nanometers, the fourth wavelength is approximately 800 nanometers, the fifth wavelength is approximately 970 nanometers, and the sixth wavelength is approximately 1210 nanometers.

As used herein, the term "memory" refers to a machine-readable medium able to store data temporarily or permanently and may be taken to include, but not be limited to, random-access memory (RAM), read-only memory (ROM), buffer memory, flash memory, and cache memory. While the machine-readable medium 622 is shown in an example embodiment to be a single medium, the term "machine-readable medium" should be taken to include a single medium or multiple media (e.g., a centralized or distributed database, or associated caches and servers) able to store instructions. The term "machine-readable medium" shall also be taken to include any medium, or combination of multiple media, that is capable of storing instructions (e.g., software) for execution by a machine (e.g., machine 600), such that the instructions, when executed by one or more processors of the machine (e.g., processor 602), cause the machine to perform any one or more of the methodologies described herein. Accordingly, a "machine-readable medium" refers to a single storage apparatus or device, as well as "cloud-based" storage systems or storage networks that include multiple storage apparatus or devices. The term "machine-readable medium" shall accordingly be taken to include, but not be limited to, one or more data repositories in the form of a solid-state memory, an optical medium, a magnetic medium, or any suitable combination thereof.

Throughout this specification, plural instances may implement components, operations, or structures described as a single instance. Although individual operations of one or more methods are illustrated and described as separate operations, one or more of the individual operations may be performed concurrently, and nothing requires that the operations be performed in the order illustrated. Structures and functionality presented as separate components in example configurations may be implemented as a combined structure or component. Similarly, structures and functionality presented as a single component may be implemented as separate components. These and other variations, modifications, additions, and improvements fall within the scope of the subject matter herein.

Certain embodiments are described herein as including logic or a number of components, modules, or mechanisms. Modules may constitute either software modules (e.g., code embodied on a machine-readable medium or in a transmission signal) or hardware modules. A "hardware module" is a tangible unit capable of performing certain operations and may be configured or arranged in a certain physical manner. In various example embodiments, one or more computer systems (e.g., a standalone computer system, a client computer system, or a server computer system) or one or more hardware modules of a computer system (e.g., a processor or a group of processors) may be configured by software (e.g., an application or application portion) as a hardware module that operates to perform certain operations as described herein.

In some embodiments, a hardware module may be implemented mechanically, electronically, or any suitable combination thereof. For example, a hardware module may include dedicated circuitry or logic that is permanently configured to perform certain operations. For example, a hardware module may be a special-purpose processor, such as a field programmable gate array (FPGA) or an ASIC. A hardware module may also include programmable logic or circuitry that is temporarily configured by software to perform certain operations. For example, a hardware module may include software encompassed within a general-purpose processor or other programmable processor. It will be appreciated that the decision to implement a hardware module mechanically, in dedicated and permanently configured circuitry, or in temporarily configured circuitry (e.g., configured by software) may be driven by cost and time considerations.

Accordingly, the phrase "hardware module" should be understood to encompass a tangible entity, be that an entity that is physically constructed, permanently configured (e.g., hardwired), or temporarily configured (e.g., programmed) to operate in a certain manner or to perform certain operations described herein. As used herein, "hardware-implemented module" refers to a hardware module. Considering embodiments in which hardware modules are temporarily configured (e.g., programmed), each of the hardware modules need not be configured or instantiated at any one instance in time. For example, where a hardware module comprises a general-purpose processor configured by software to become a special-purpose processor, the general-purpose processor may be configured as respectively different special-purpose processors (e.g., comprising different hardware modules) at different times. Software may accordingly configure a processor, for example, to constitute a particular hardware module at one instance of time and to constitute a different hardware module at a different instance of time.

Hardware modules can provide information to, and receive information from, other hardware modules. Accordingly, the described hardware modules may be regarded as being communicatively coupled. Where multiple hardware modules exist contemporaneously, communications may be achieved through signal transmission (e.g., over appropriate circuits and buses) between or among two or more of the hardware modules. In embodiments in which multiple hardware modules are configured or instantiated at different times, communications between such hardware modules may be achieved, for example, through the storage and retrieval of information in memory structures to which the multiple hardware modules have access. For example, one hardware module may perform an operation and store the output of that operation in a memory device to which it is communicatively coupled. A further hardware module may then, at a later time, access the memory device to retrieve and process the stored output. Hardware modules may also initiate communications with input or output devices, and can operate on a resource (e.g., a collection of information).

The various operations of example methods described herein may be performed, at least partially, by one or more processors that are temporarily configured (e.g., by software) or permanently configured to perform the relevant operations. Whether temporarily or permanently configured, such processors may constitute processor-implemented modules that operate to perform one or more operations or functions described herein. As used herein, "processor-implemented module" refers to a hardware module implemented using one or more processors.

Similarly, the methods described herein may be at least partially processor-implemented, a processor being an example of hardware. For example, at least some of the operations of a method may be performed by one or more processors or processor-implemented modules. Moreover, the one or more processors may also operate to support performance of the relevant operations in a "cloud computing" environment or as a "software as a service" (SaaS). For example, at least some of the operations may be performed by a group of computers (as examples of machines including processors), with these operations being accessible via a network (e.g., the Internet) and via one or more appropriate interfaces (e.g., an application program interface (API)).

The performance of certain of the operations may be distributed among the one or more processors, not only residing within a single machine, but deployed across a number of machines. In some example embodiments, the one or more processors or processor-implemented modules may be located in a single geographic location (e.g., within a home environment, an office environment, or a server farm). In other example embodiments, the one or more processors or processor-implemented modules may be distributed across a number of geographic locations.

Some portions of this specification are presented in terms of algorithms or symbolic representations of operations on data stored as bits or binary digital signals within a machine memory (e.g., a computer memory). These algorithms or symbolic representations are examples of techniques used by those of ordinary skill in the data processing arts to convey the substance of their work to others skilled in the art. As used herein, an "algorithm" is a self-consistent sequence of operations or similar processing leading to a desired result. In this context, algorithms and operations involve physical manipulation of physical quantities. Typically, but not necessarily, such quantities may take the form of electrical, magnetic, or optical signals capable of being stored, accessed, transferred, combined, compared, or otherwise manipulated by a machine. It is convenient at times, principally for reasons of common usage, to refer to such signals using words such as "data," "content," "bits," "values," "elements," "symbols," "characters," "terms," "numbers," "numerals," or the like. These words, however, are merely convenient labels and are to be associated with appropriate physical quantities.

Unless specifically stated otherwise, discussions herein using words such as "processing," "computing," "calculating," "determining," "presenting," "displaying," or the like may refer to actions or processes of a machine (e.g., a computer) that manipulates or transforms data represented as physical (e.g., electronic, magnetic, or optical) quantities within one or more memories (e.g., volatile memory, non-volatile memory, or any suitable combination thereof), registers, or other machine components that receive, store, transmit, or display information. Furthermore, unless specifically stated otherwise, the terms "a" or "an" are herein used, as is common in patent documents, to include one or more than one instance. Finally, as used herein, the conjunction "or" refers to a non-exclusive "or," unless specifically stated otherwise.

What is claimed is:

1. A system, comprising:

a light emitter configured to emit light at a first wavelength over a range of approximately 900 to 1000 nanometers and at a second wavelength over a range of approximately 1300 to 1400 nanometers;

a first light detector spaced at a first distance from the light emitter;

a second light detector spaced at a second distance from the light emitter, the second distance approximately twice the first distance; and a processor configured to determine a glycogen level of muscle tissue as a function of hydration of the muscle tissue, wherein the first wavelength is selected to correspond to a water absorption peak in the muscle tissue and the second wavelength is selected to have a higher water absorption coefficient in the muscle tissue than the first wavelength such that differential backscatter light detected at the first and second wavelengths reflects differential absorption by water in the muscle tissue as a function of glycogen-bound water content, the processor determining the glycogen level based on:

determining a first ratio based on a differential relationship between backscatter light as detected by the first and second light detectors at the first wavelength;

determining a second ratio based on a differential relationship between backscatter light as detected by the first and second light detectors at the second wavelength; and comparing the first and second ratios to look-up table ratios to identify a closest one of the look-up table ratios to the first and second ratios as determined, each look-up table ratio corresponding to a predetermined glycogen level, the predetermined glycogen level of the closest one of the look-up table ratios being the glycogen level of the muscle tissue.

2. The system of claim 1, wherein the muscle tissue is in a muscle layer below layers of non-muscle tissue, the muscle layer having a depth from a skin surface, and wherein the second distance is approximately twice the depth of the muscle layer from the skin surface.

3. The system of claim 2, wherein the first distance is approximately 12.5 millimeters and the second distance is approximately 25 millimeters.

4. The system of claim 1, wherein the light emitter comprises a first light emitting diode (LED) configured to emit light at the first wavelength and a second LED configured to emit light at the second wavelength.

5. The system of claim 1, wherein the light emitter is further configured to emit light at wavelengths between approximately 660 and approximately 820 nanometers;

wherein at least one of the first light detector and the second light detector is configured to detect backscatter light from the light between approximately 660 and approximately 820 nanometers; and wherein the processor is configured to determine an oxygen level of hemoglobin in blood based on the backscatter light from the light between approximately 660 and approximately 820 nanometers.

6. The system of claim 5, wherein the light emitter comprises a first light emitting diode (LED) configured to emit light at the first wavelength, a second LED configured to emit light at the second wavelength, and four LEDs configured to emit the light between approximately 660 and approximately 820 nanometers.

7. The system of claim 1, wherein the first and second light detectors are photodiodes.

8. The system of claim 1, wherein the light emitter and first and second light detectors are positioned on a wearable device configured to be positioned on and secured to a forearm of a user proximate an elbow of the user.

9. The system of claim 1, wherein the processor is further configured to cause a user interface to display information related to the glycogen level of the muscle tissue.

10. The system of claim 9, wherein the light emitter and the first and second light detectors are components of a wearable device and the processor is a component of an external device different than the wearable device.

11. The system of claim 9, wherein the light emitter, the first and second light detectors, and the processor are components of a wearable device.

12. The system of claim 1, wherein the first wavelength is approximately 970 nanometers and the second wavelength is approximately 1310 nanometers.

13. The system of claim 1, wherein the light emitter is further configured to emit light at a third wavelength, a fourth wavelength, a fifth wavelength, and a sixth wavelength, and further comprising:

a third light detector spaced between the light emitter and the first light detector;

wherein the processor is configured to determine the glycogen level of the muscle tissue as the function of hydration of the muscle tissue based on a relationship between backscatter light from the muscle tissue and the non-muscle tissue as detected by the first, second, and third light detectors.

14. The system of claim 13, wherein the third wavelength is approximately 680 nanometers, the fourth wavelength is approximately 800 nanometers, the fifth wavelength is approximately 970 nanometers, and the sixth wavelength is approximately 1210 nanometers.

15. A wearable device, comprising:

a light emitter configured to emit light at a first wavelength over a range of approximately 900 to 1000 nanometers and at a second wavelength over a range of approximately 1300 to 1400 nanometers;

a first light detector spaced at a first distance from the light emitter;

a second light detector spaced at a second distance from the light emitter, the second distance approximately twice the first distance; and a processor configured to determine a glycogen level of muscle tissue as a function of hydration of the muscle tissue, wherein the first wavelength is selected to correspond to a water absorption peak in the muscle tissue and the second wavelength is selected to have a higher water absorption coefficient in the muscle tissue than the first wavelength such that differential backscatter light detected at the first and second wavelengths reflects differential absorption by water in the muscle tissue as a function of glycogen-bound water content, the processor determining the glycogen level based on:

determining a first ratio based on a differential relationship between backscatter light as detected by the first and second light detectors at the first wavelength;

determining a second ratio based on a differential relationship between backscatter light as detected by the first and second light detectors at the second wavelength; and comparing the first and second ratios to look-up table ratios to identify a closest one of the look-up table ratios to the first and second ratios as determined, each look-up table ratio corresponding to a predetermined glycogen level, the predetermined glycogen level of the closest one of the look-up table ratios being the glycogen level of the muscle tissue.

16. The wearable device of claim 15, wherein the muscle tissue is in a muscle layer below layers of non-muscle tissue, the muscle layer having a depth from a skin surface, and wherein the second distance is approximately twice the depth of the muscle layer from the skin surface.

17. The wearable device of claim 16, wherein the first distance is approximately 12.5 millimeters and the second distance is approximately 25 millimeters.

18. The wearable device of claim 15, wherein the light emitter comprises a first light emitting diode (LED) configured to emit light at the first wavelength and a second LED configured to emit light at the second wavelength.

19. The wearable device of claim 15, wherein the light emitter is further configured to emit light at wavelengths between approximately 660 and approximately 820 nanometers;

wherein at least one of the first light detector and the second light detector is configured to detect backscatter light from the light between approximately 660 and approximately 820 nanometers; and wherein the processor is further configured to determine an oxygen level of hemoglobin in blood based on the backscatter light from the light between approximately 660 and approximately 820 nanometers.

20. The wearable device of claim 19, wherein the light emitter comprises a first light emitting diode (LED) configured to emit light at the first wavelength, a second LED configured to emit light at the second wavelength, and four LEDs configured to emit the light between approximately 660 and approximately 820 nanometers.

21. The wearable device of claim 15, wherein the first and second light detectors are photodiodes.

22. The wearable device of claim 15, wherein the light emitter and first and second light detectors are positioned on a wearable device configured to be positioned on and secured to a forearm of a user proximate an elbow of the user.

23. The wearable device of claim 15, wherein the processor is further configured to cause a user interface to display information related to the glycogen level of the muscle tissue.

24. The wearable device of claim 15, wherein the first wavelength is approximately 970 nanometers and the second wavelength is approximately 1310 nanometers.

25. The wearable device of claim 15, wherein the light emitter is further configured to emit light at a third wavelength, a fourth wavelength, a fifth wavelength, and a sixth wavelength, and further comprising:

a third light detector spaced between the light emitter and the first light detector;

wherein the processor is configured to determine the glycogen level of the muscle tissue as the function of hydration of the muscle tissue based on a relationship between backscatter light from the muscle tissue and the non-muscle tissue as detected by the first, second, and third light detectors.

26. The wearable device of claim 25, wherein the third wavelength is approximately 680 nanometers, the fourth wavelength is approximately 800 nanometers, the fifth wavelength is approximately 970 nanometers, and the sixth wavelength is approximately 1210 nanometers.

* * * * *